US009982254B2

(12) United States Patent
Nemoto et al.

(10) Patent No.: US 9,982,254 B2
(45) Date of Patent: May 29, 2018

(54) LIGAND HAVING THREE FINGER STRUCTURE AND A METHOD FOR DETECTING A MOLECULE BY USING THEREOF

(71) Applicants: Saitama University, Saitama, Saitama (JP); Nikon Corporation, Chiyoda-ku, Tokyo (JP)

(72) Inventors: Naoto Nemoto, Saitama (JP); Yuuya Yotsumoto, Saitama (JP)

(73) Assignees: Saitama University, Saitama (JP); Nikon Corporation, Tokyo (JP)

( * ) Notice: Subject to any disclaimer, the term of this patent is extended or adjusted under 35 U.S.C. 154(b) by 507 days.

(21) Appl. No.: 14/279,788

(22) Filed: May 16, 2014

(65) Prior Publication Data

US 2015/0031564 A1 Jan. 29, 2015

Related U.S. Application Data

(63) Continuation of application No. PCT/JP2012/080000, filed on Nov. 19, 2012.

(30) Foreign Application Priority Data

Nov. 18, 2011 (JP) ................................ 2011-253311

(51) Int. Cl.
*C07K 14/435* (2006.01)
*C12N 15/10* (2006.01)
*C07K 14/47* (2006.01)

(52) U.S. Cl.
CPC ........ *C12N 15/1062* (2013.01); *C07K 14/435* (2013.01); *C07K 14/4702* (2013.01)

(58) Field of Classification Search
CPC ............. C07K 14/435; C07K 14/4702; C12N 15/1062
See application file for complete search history.

(56) References Cited

PUBLICATIONS

Torres (Biochemical Journal 360(3), 539-548, 2001).*
Yamada et al., "Tumor Markers of Malignant Lymphoma and Their Molecular Characteristics and Functions," JJCLA, 2007, 32(2):169-173, full English translation, 9 pages.

* cited by examiner

*Primary Examiner* — Julie Ha
*Assistant Examiner* — Li N Komatsu
(74) *Attorney, Agent, or Firm* — Foley & Lardner LLP

(57) ABSTRACT

The present invention improves in vitro virus synthesis efficiency and stability of mRNA derived from screened cDNA in a cDNA display method to improve the efficiency and reliability of the production of a peptide by a molecular evolutionary engineering technique. Provided is a ligand which comprises three fingers formed from antiparallel β-sheets and a loop region intercalated between the antiparallel β-sheets, wherein at least a fingertip part formed by the loop region of each of the fingers is bound to the target molecule, and wherein the ligand comprises the amino acid sequence of SEQ ID NO: 1. In the amino acid sequence of SEQ ID NO: 1, X7 represents an arbitrary amino acid residue that constitutes the fingertip part of each of the fingers, each numeric character represents the number of amino acid residues, and X7 and X4 are not composed of the same amino acid residues as each other.

11 Claims, 11 Drawing Sheets

Bucandin
(Bucandin)
36 Å
12 Å
24 Å

Erabutoxin
(Erabutoxin-a)

Toxin-α
(Toxin-α)

Candoxin
(Candoxin)

LIGAND HAVING THREE FINGER STRUCTURE AND A METHOD FOR DETECTING A MOLECULE BY USING THEREOF

RELATED APPLICATION

This application is a continuation application of international patent application No. PCT/JP2012/080000 filed on Nov. 19, 2012, which claims priority from JP Application 2011-253311, filed on Nov. 18, 2011, the entire disclosures of which are incorporated by reference.

SEQUENCE LISTING

The instant application contains a Sequence Listing which has been submitted electronically in ASCII format and is hereby incorporated by reference in its entirety. Said ASCII copy, created on Oct. 17, 2014, is named 107986-0102_SL.txt and is 20,951 bytes in size.

BACKGROUND OF THE INVENTION

The present invention relates to a ligand having three finger structure, and a method for detecting a particular molecule by using thereof.

BACKGROUND ART

Recently, antigen-antibody reaction using their reaction specificity is employed in screening or detection of proteins. When the antibody-antigen reaction is used, the antibody should be obtained by using the protein to be the antigen. However, the antibody is often not obtained caused by the size of the molecular weight. Alternatively, even if the antibody is obtained, it takes time and extra work for purifying the antibody that binds to a specific epitope. Also, the antigen binds to the antibody highly specifically, and generally tightly.

Proteins having different structure from antibodies include α-neurotoxin (α-neurotoxin), of which molecular weight is not large as those of the antibodies. α-Neurotoxin is a protein group found in snake toxin of venom including those belonging to elapidae; and is a small size protein being composed of 60 to 70 amino acids (MW: 7 to 8 kDa). Several proteins among them generally include three finger-like scaffold in common which comprises 4 to 5 of disulfide bonds, 3 to 5 of anti-parallel β-sheet, and three projection loops that form the three finger structure (Endo T, Tamiya N. (1987), Pharmacol Ther., 34, 403-451 (Non-patent document 1)).

Since the scaffold is formed by using the disulfide bonds, it is referred to as a disulfide framework. Its form is highly-conserved even when the amino acid residues composed of the β-sheet are changed. Also, the amino acids involving in a natural receptor are conserved (Antil, S., Servent, D. and Menez, A. (1999). J. Biol. Chem., 274, 34851-34858 (Non-patent document 2); Teixeira-Clerc F, Menez A, Kessler P. (2002) J. Biol. Chem., 277, 25741-25747 (Non-patent document 3)).

It is known that the protein scaffold is small sized, highly heat stable for resisting the temperature from 60 to 70° C. (Sivaraman T, Kumar T K, Hung K W, Yu C. Biochemistry. 2000 Aug. 1; 39 (30):8705-10. (Non-patent document 4)), and have very high specificity to their receptors (the protein) (Antil, S., Servent, D. and Menez, A. (1999), J. Biol. Chem., 274, 34851-34858 (Non-patent document 5)).

Furthermore, Nygren, P-A and Skerra, A. ((2004), J. Immunol. Methods., 290, 3-28 (Non-patent document 6)) disclose the trial to generate a combinatorial library of proteins to find a new protein instead of the antibody (herein below, it is referred to as the "prior art 1").

Also, JP 2007-306866 A (Patent document 1) discloses the art to produce the protein which specifically bind to Interleukin-6 receptor (it is sometimes referred to as "IL-6R") by partially changing the loop of CTx3 having the three finger-like scaffold (it is referred to as the "prior art 2").

REFERENCES

1. JP 2007-306866 A
2. Endo T, Tamiya N. (1987), Pharmacol Ther., 34, 403-451
3. Antil, S., Servent, D. and Menez, A. (1999). J. Biol. Chem., 274, 34851-34858
4. Teixeira-Clerc F, Menez A, Kessler P. (2002) J. Biol. Chem., 277, 25741-25747
5. Sivaraman T, Kumar T K, Hung K W, Yu C. Biochemistry. 2000 Aug. 1; 39 (30):8705-10.
6. Antil, S., Servent, D. and Menez, A. (1999), J. Biol. Chem., 274, 34851-34858
7. Nygren, P-A and Skerra, A. (2004), J. Immunol. Methods., 290, 3-28

SUMMARY OF THE INVENTION

Meanwhile, an intermolecular interaction occurs between molecules having high molecular weight such as a general receptor and the target protein, and also between that and a variety of spheroprotein having low molecular weight or low molecular-weight compound. Since the scaffold which is capable of interaction between the low molecular-weight protein and compound has a variety of applications, there are social needs for creating such a scaffold. Particularly, when the target of such scaffolds is a marker protein for much disease, they contribute early detection of the disease. Therefore, there are particular strong needs from the view point of preventive medicine.

The first feature of the present invention is a ligand having three fingers, each of which comprises anti-parallel β sheet parts and a loop area sandwiched them, and at least the loop area which forms fingertip part binds the target molecule, comprising the following amino acid sequence:

```
                                          (SEQ ID NO: 1)
MECYR(X7)LKITCSAEETFCYKWLNK(X4)RWLGCAKTCTEID

(X2)NVYNKCCTTNLCNT,
```

wherein X represents an arbitrary amino acid being composed of the sequence, and each number represents the amino acid numbers. X7 is not composed of particular amino acids, and X4 is not composed of particular amino acids. Also wherein, number of cysteine in the SEQ ID NO: 1 is 8. In the SEQ ID NO: 1, X7 does not become the sequence of GVSGCH (SEQ ID NO: 26), X4 does not become that of ISNE (SEQ ID NO: 27), and X2 does not become that of TW at the same time.

Also, among the amino acid sequences of the fingertips, X7 is anyone of the sequences selected from the following group (A); X4 is anyone of the sequences selected from the following group (B); and X2 is anyone of the sequences selected from the following group (C). Entire of the sequence is a combination of the amino acid sequences selected from the groups as mentioned above.

(A) PTQPKRT (SEQ ID NO: 2), PNPADRN (SEQ ID NO: 4), NPPTSDT (SEQ ID NO: 6), PEVDIRQ (SEQ ID NO: 8), ETNNGQP (SEQ ID NO: 10), RRSMHTV (SEQ ID NO: 12) and PRTIRA (SEQ ID NO: 14);

(B) GTRQ (SEQ ID NO: 3), NPSH (SEQ ID NO: 5), PGNT (SEQ ID NO: 7), KLPR (SEQ ID NO: 9), TIPA (SEQ ID NO: 11), IAKN (SEQ ID NO: 13) and DLAE (SEQ ID NO: 15);

(C) PP, NR, TQ, KP, ER, TP and NQ.

Also, X7, X4 and X2 of the amino acid sequences of the fingertips are anyone of the combination selected from the following groups (a) to (f) and (g).

(a) PTQPKRT (SEQ ID NO: 2), GTRQ (SEQ ID NO: 3), PP;

(b) PNPADRN (SEQ ID NO: 4), NPSH (SEQ ID NO: 5), NR;

(c) NPPTSDT (SEQ ID NO: 6), PGNT (SEQ ID NO: 7), TQ;

(d) PEVDIRQ (SEQ ID NO: 8), KLPR (SEQ ID NO: 9), KP;

(e) ETNNGQP (SEQ ID NO: 10), TIPA (SEQ ID NO: 11), ER;

(f) RRSMHTV (SEQ ID NO: 12), IAKN (SEQ ID NO: 13), TP;

(g) NPRTIRA (SEQ ID NO: 14), DLAE (SEQ ID NO: 15), NQ.

Here, the term, the "target molecule" is selected from the group consisting of survivin monomer, survivin dimer and low molecular-weight compound, and preferably survivin monomer or survivin dimer. Here, the term, "low molecular-weight compound" means the compound having the molecular weight of which range is 30 to 1,500 with or without sugar chain. For example, there are mentioned such as aflatoxin B1, ciguatoxin, fluorescein, N-acetyl-D-glucosamine and the like. The ligand of the present invention may be survivin binding ligand having the above-mentioned structure. The ligand may exist as a corresponding form to a polynucleotide being coded by the ligand, and the ligand is binding to the polynucleotide coding the ligand through puromycin.

The second aspect of the present invention is a ligand having three fingers, each of which comprises anti-parallel β sheet parts and a loop area sandwiched them, and at least the loop area which forms fingertip part binds the target molecule, comprising the following amino acid sequence.

```
                                   (SEQ ID NO: 16)
MECYR(X6)LKITCSAEETFCYKWLNK(X4)RWLGCAKTCTEID

(X2)NVYNKCCTTNLCNT
```

wherein X represents an arbitrary amino acid being composed of the fingertip part, and each number represents the number of amino acids. Both X6 and X4 are not composed of single amino acids. Namely, X6 is not composed of particular amino acids, and X4 is not composed of particular amino acids.

Among the amino acid sequences of the fingertips, X6 is anyone of the sequences selected from the following group (A'), X4 is anyone of the sequences selected from the following group (B), and X2 is anyone of the sequences selected from the following group.

(A') In the sequence being composed of 7 amino acids among PTQPKRT (SEQ ID NO: 2), PNPADRN (SEQ ID NO: 4), NPPTSDT (SEQ ID NO: 6), PEVDIRQ (SEQ ID NO: 8), ETNNGQP (SEQ ID NO: 10), RRSMHTV (SEQ ID NO: 12) and PRTIRA (SEQ ID NO: 14), one of the amino acid is deleted from each sequence, and composed of 6 amino acids;

(B) GTRQ (SEQ ID NO: 3), NPSH (SEQ ID NO: 5), PGNT (SEQ ID NO: 7), KLPR (SEQ ID NO: 9), TIPA (SEQ ID NO: 11), IAKN (SEQ ID NO: 13) and DLAE (SEQ ID NO: 15);

(C) PP, NR, TQ, KP, ER, TP and NQ.

Here, the phrase "one of the amino acid is deleted from each sequence" means, for example, when the amino acid sequence is that of SEQ ID NO: 2, one arbitrary amino acid is deleted from the sequence PTQPKRT (SEQ ID NO: 2), namely, they show one of those among TQPKRT £SEQ ID NO: 28), PQPKRT (SEQ ID NO: 29), PTPKRT (SEQ ID NO: 30), PTQKRT (SEQ ID NO: 31), PTQPRT (SEQ ID NO: 32), PTQPKT (SEQ ID NO: 33), and PTQPKR (SEQ ID NO: 34). Alternatively, the "target molecule", the "low molecular-weight compound" and the ligand are as described above.

The third aspect of the present invention is a method for detecting a disease marker comprising the steps of: (a) preparing a ligand according to the claim 1 or 7; (b) forming a ligand-target molecule conjugate by contacting the ligand and a specimen; (c) choosing the ligand-target molecule conjugate; and (d) calculating the concentration of the chosen target molecule in the specimen. Here, the target molecule is selected from the group consisting of survivin monomer, survivin dimer, and low molecular-weight compound. The low molecular-weight compound is as described above.

Furthermore, the disease is one selected from the group consisting of a tumor, infectious disease, and food poisoning. Here, the tumor is classified into benign tumor, which is generally growing slow without invasion into surrounding tissue, and neoplasm, in which primary tumor has invasion into the surrounding tissue and forms metastatic foci to give adverse effects to a host with invasion. Histologically, they are classifying into the benign tumor such as papilloma, adenoma, cystoma, squamous cystoma, transitional cytoma, and others, the neoplasm such as planocellular carcinoma, adenocarcinoma, transitional cell carcinoma, hepatoma, undifferentiated carcinoma and others.

Anatomically, there may be mentioned, for example, head and neck cancer such as maxillary cancer, pharyngeal cancer, laryngeal cancer and others; breast cancer such as thyroid cancer, mammary cancer, lung cancer and others; gastroenterological cancer such as esophageal cancer, stomach cancer, duodenal carcinoma, colon cancer, rectal cancer, pancreatic cancer, hepatoma, and others; urologic cancer such as renal cancer, bladder cancer, prostate cancer, and others; genital tumor such as uterus cancer, ovary cancer and others; skin cancer such as basal cell carcinoma, squamous cell carcinoma and others; benign neurogenic tumor such as choroid plexus papilloma, neurilemmoma, astrocytoma, neurofibroma, melanocytic lentigo, meningioma and others; malignant neurogenic tumor such as neuroblastoma, malignant pheochromocytoma, melanoma, malignant neurilemoma and others.

Infectious diseases are classified into bacterial infection, rickettsial infection, fungus infection, parasitic protozoan infection, viral infection and others. There may be mentioned, for example, bacterial infection such as tuberculosis, cholera, diphtheria, dysentery, scarlatina, legionellosis, Lyme disease, Q-fever and others; rickettsial infection such as typhous, trombiculiasis and others; fungus disease such as aspergillosis, candidiasis, cryptococcosis, *pneumocystis carinii* pneumonia and others; parasitic protozoan infection such as amoebic dysentery, malaria and others; viral infection caused by viruses such as influenza, viral hepatitis, measles, varicella, rubella, polio, dengue fever, rabies, West Nile fever.

Food poisoning is classified into toxin type food poisoning, which is often caused by taking harmful or toxic agents included in foods and the like, infection type, which is caused by microbial infection, and intermediate type. As the toxin type, there are mentioned, for example, such as enterotoxin, botulinus toxin, tetrodotoxin, aflatoxin, verotoxin, toxins contained in fungi and the like. As the infection type, there are mentioned, for example, such as *Vibrio parahaemolyticus, salmonella*, and other bacterial infection.

The fourth aspect of the present invention is a screening method of prey protein comprising the steps of: (a) forming a mRNA-linker conjugate a linker for a ligand evolution and mRNA having complementary sequence by using RNA ligase at a mRNA binding site; (b) producing a linker-protein-mRNA conjugate wherein a protein having an enzyme activity is synthesized from cDNA synthesized by reverse transcription reaction with the mRNA as a template to obtain the linker-protein-mRNA conjugate on which the protein is bound at a protein binding site of the linker; (c) forming bait protein wherein mRNA is digested to obtain the bait protein which can be bound to a solid phase; (d) immobilizing the bait protein wherein a predetermined molecule bound to the solid phase binding site of the bait protein is ligated to the predetermined molecule immobilized on the solid phase; (e) reacting the bait protein and the labelled prey protein to generate a bait protein-prey protein conjugate; (f) collecting the bait protein-prey protein conjugate; and (g) eluting the prey protein by washing the collected bait protein-prey protein conjugate.

Here, the linker comprises a main chain and a side chain. The main chain has a side chain binding site, being located closely to the 3' terminal, for binding the side chain which functions as a spacer for puromycin, and a solid phase binding site, being located to the 5' terminal side, for binding a predetermined molecule to form the binding with the solid phase. The side chain has a label binding site to bind the label, to which the label is bound, and the terminal which is not bound to the main chain is bound to puromycin.

The side chain may be formed by using an arbitrary base sequence or polyethylene glycol spacer, and the predetermined molecule may be biotin. Also, the ligation enzyme may be T4 RNA ligase. Furthermore, the solid phase may be the magnetic bead, and it may be collected by using magnetic force in the collection step.

The protein which interact the particular protein or the protein fragment used as bait protein is screened from a library. During the screening, the protein being used as the bait is referred to as "bait" and that being caught is referred to as "prey". Here, as the bait protein, the ligand as mentioned above and other desirable proteins may be used. Also, the prey protein is selected from the group consisting of, for example, survivin monomer, survivin dimer, and low molecular-weight compounds. It may be survivin monomer or survivin dimer. Here, the above mentioned "low molecular-weight compounds" is defined as those having the molecular weight of which range is 30 to 1,500, with our without sugar chain. For example, there are mentioned, for example, aflatoxin B1, ciguatoxin, fluorescein, N-acetyl-D-glucosamine and the like.

According to the present invention, the ligand which functions as the target molecule, the antagonist, or the agonist may be obtained. Alternatively, they may be produced lower cost compared to produce the antibody. Also, according to the present invention, the marker of the disease may be detected rapidly and accurately. Furthermore, according to the present invention, the prey protein which desirably interacts with the bait protein may be obtained by using rapid and convenient screening method.

BRIEF EXPLANATIONS FOR DRAWINGS

Figure 10:
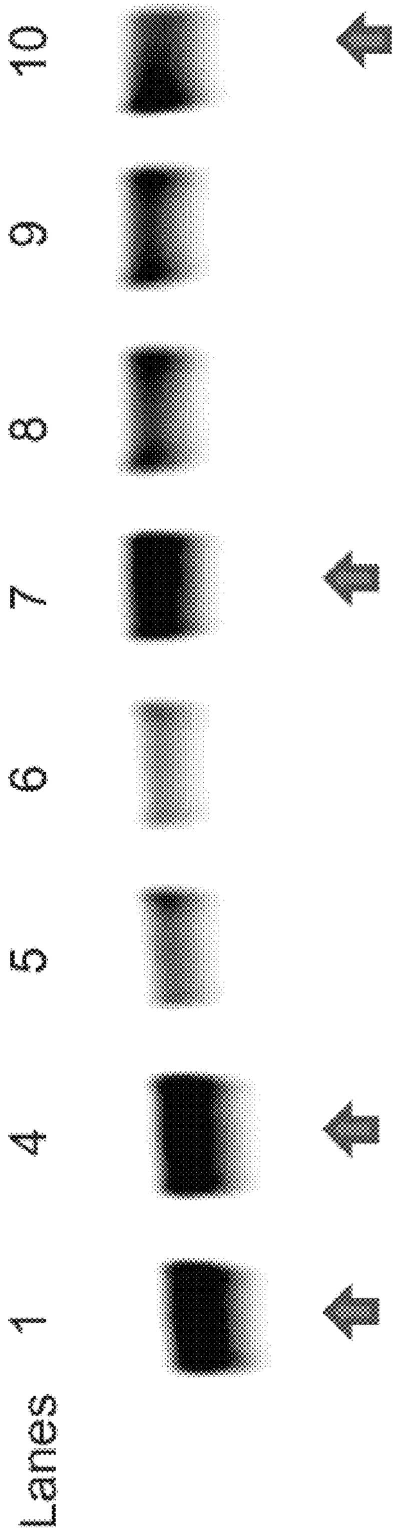
Figure 11:
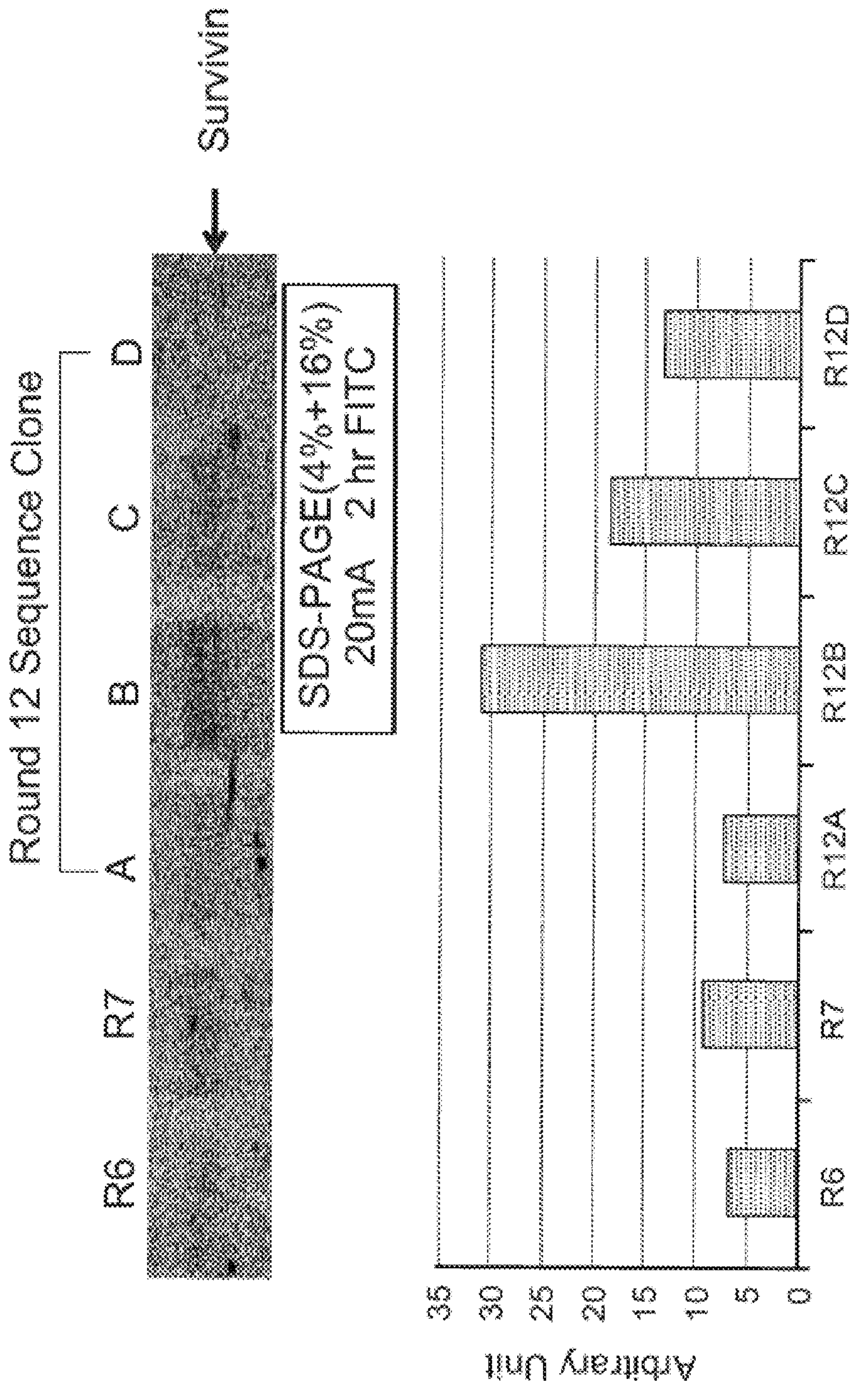

FIG. 10 is the image of gel electrophoresis showing status of the ligand and the target molecule obtained in the round 7; and FIG. 11 is image of gel electrophoresis showing status of the ligand and the target molecule obtained in the round 6 (R6), the round 7 (R7), and the round 12 (R12), as well as the relative activities of them.

EMBODIMENT FOR CARRYING OUT THE INVENTION

The present invention is explained more detail by using FIGS. 1 to 9 here in below. In the present specification, a conserved cysteine, which is included in the amino acid sequence of the three finger-like scaffold to form disulfide bond, is shown as C1 to C8 from the N-terminal of the sequence.

Alternatively, the terms "exist as corresponding form" is defined that both the protein and the polynucleotide coding thereof corresponding exist a manner of the form at one-on-one. Such corresponding technique is called as a display technique, and a variety of techniques are known. As the corresponding technique using a cell free translation system, there are mentioned, for example, such as ribosome display method, STABLE method (non-covalent bond DNA display method), micro beads droplet method, covalent bond DNA display method and the like, and cDNA display (in vitro virus method) used in the present invention is also included. In the in vitro method, the ligand binds to, for example, the polynucleotide coding thereof through puromycin. Also, it may include pairs of the polynucleotide coding the ligand in each phage or a cell as the same as display methods such as phage display method, yeast display method, bacteria display method, and the like.

Figure 1:
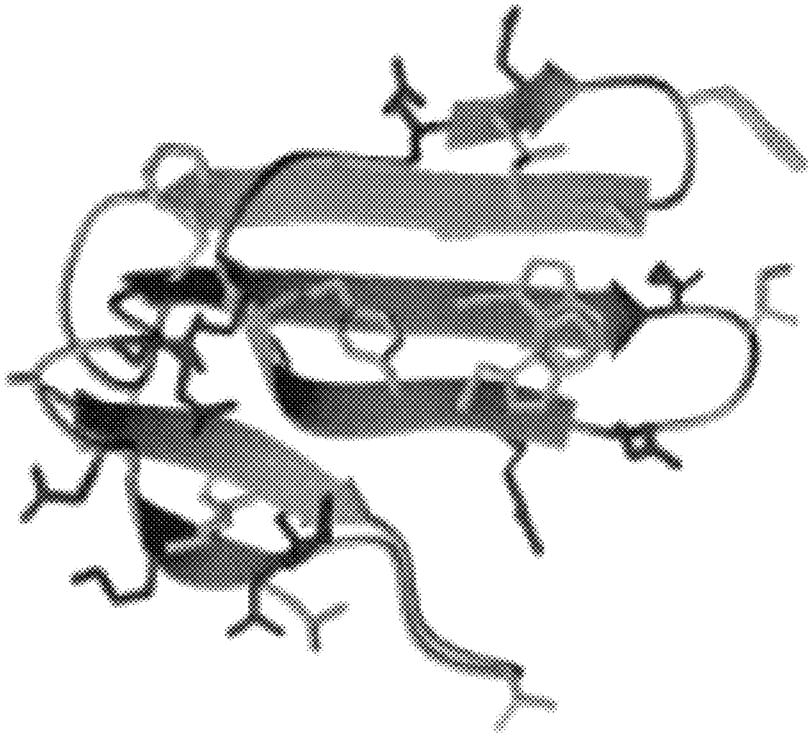
FIG. 1 is a schematic drawing showing the ligand of the present invention.

FIG. 1 schematically shows the present ligand having the three finger scaffold. In FIG. 1, the part shown by the wide arrow shows β-sheet structure part, and each finger is shown sequentially as the number L1 to L3 from the 5' terminal. In FIG. 1, the direction of β-sheet structure part of L1 goes opposite direction to that of L2, clearly shown as the direction of the arrow showing the β-sheet direction.

Namely, the ligand of the first aspect of the present invention comprises (A) β-sheets of which directions are opposite (anti-parallel β-sheets) (B) loop area sandwiched between them respectively, (C) which has a following amino acid sequence for binding to a target molecule through fingertips being composed of the loop area. The ligand of the present invention has anyone of the following amino acid sequences.

```
                                          (SEQ ID NO: 1)
MECYR(X7)LKITCSAEETFCYKWLNK(X4)RWLGCAKTCTEID

(X2)NVYNKCCTTNLCNT

                                         (SEQ ID NO: 16)
MECYR(X6)LKITCSAEETFCYKWLNK(X4)RWLGCAKTCTEID

(X2)NVYNKCCTTNLCNT
```

wherein X represents an arbitrary amino acid and the number represents the number of the amino acids. Therefore, among the above mentioned amino acids, X7 represents the sequence composed of 7 amino acids, X6 represents the sequence composed of 6 amino acids, X4 represents the sequence composed of 4 amino acids, and X2 represents the sequence amino acids composed of 2 amino acids, respectively. Here, there are mentioned as the protein having the three finger scaffold (it is defined as "3FS" herein below), for example, those shown in the following Table 1.

TABLE 1

| Name of neurotoxin | Accession No. | Amino acid numbers | Biological sources |
|---|---|---|---|
| Erabutoxin-a | P60615 | 95 | Laticauda semifasciata |
| Toxin-α | — | 61 | Naja nigricollis |
| Candoxin | — | 71 | Malayan krait Bungarus candidus |
| CTx3 | — | 61 | Micrurus corallinus |
| Bucandin | — | 63 | Malayan krait (Bungarus candidus) |

Figures 2A, 2B, 2C, 2D:
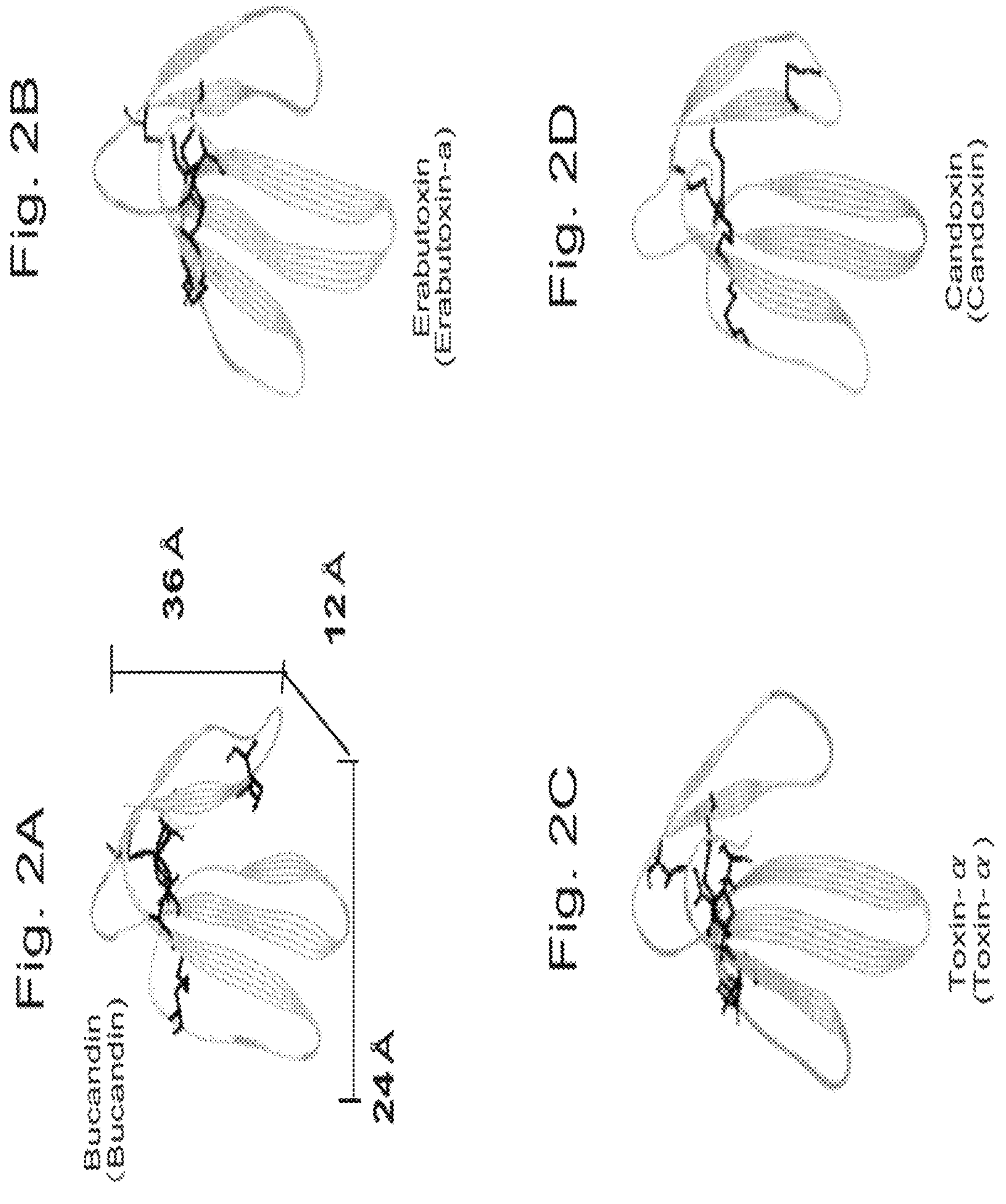
FIG. 2 is the schematic drawing showing structures of bucandin (A) in contrast with other three finger scaffold (Erabutoxin-a (B), Toxin-a (C), Candoxin (D))

Among the neurotoxin shown in the Table 1, the structures of Erabutoxin-a (Erabutoxin-a), Toxin-α (Toxin-α), Candoxin (Candoxin) and Bucandin (Bucandin) are schematically shown in FIGS. 2A to 2D. Among them, the proteins except Bucandin, all of them are shown in FIG. 2A, are known that they have large differences among the lengths of three fingers, high specificity of the target molecule, and low specificity to the low molecular. In contrast, the three finger lengths and entire molecular size of bucandin is different from other 3 neurotoxins. Bucandin has a small differences among three fingers, and it is considered to improve recognition performance for the lower molecular. Therefore, it may be used as the protein having 3F.

Bucandin is a peptide isolated from venom of *Bungarus candidus* belonging to Malayan *Bungarus multicinctus*, is composed of 63 amino acids, The protein is neurotoxin and cytotoxin, has platelet aggregation inhibition activity, and it functions as an ion channel blocker.

Also, the fingertip parts of the loop area of L1 to L3 may be randomized by using cDNA display method. Because, 3F-cDNA display method is suitable for generating and choosing a variety of the ligand; evolution speed of 1 round, which is defined as such a series of events; and furthermore, modified bucandin is effectively obtained by forming disulfide bonds through the oxidization process for reliable reverse transcription.

Here, the term, "randomization", is defined that original amino acid sequence of bucandin is replaced with different amino acid sequence in the predetermined position of the protein. Both of X7 and X4 does not contain the sequence, in which each amino acid is replaced by single variety of the same amino acid, for example, A, R, N, P, and the like.

Also, depending on the sequencing information obtained in a certain round, it is possible to randomize the amino acid on the specific position of the amino acid sequence without changing other amino acids on other positions of the sequence.

The target molecule is defined as the arbitrary molecule to which the ligand of the present invention can bind, there are mentioned such as, for example, proteins, glycoproteins, sugars, nucleic acids, a variety of low molecular-weight compounds and the like. For example, there are mentioned such as a variety of receptors, surface antigens of viruses or cells, antibodies, hormones, DNA, RNA and the like. The binding between the proteins and the target molecule may be anyone of following bonding: hydrophobic binding, electrostatistic bonding, hydrogen bonding, and van der Waals binding.

The target molecule of the ligand of the present invention may be the low molecular peptide selected from the group consisting of survivin monomer, survivin dimer, and low molecular-weight compounds. Among them, survivin is an inhibitor of apoptosis protein (IAP, a group of protein which inhibits caspase as a proteolytic component in apoptotic pathway). Then, it is known that it is highly frequently expressed in the cancer cell, and also said that it is associated to the resistance to an anti-cancer agent.

Figure 4:
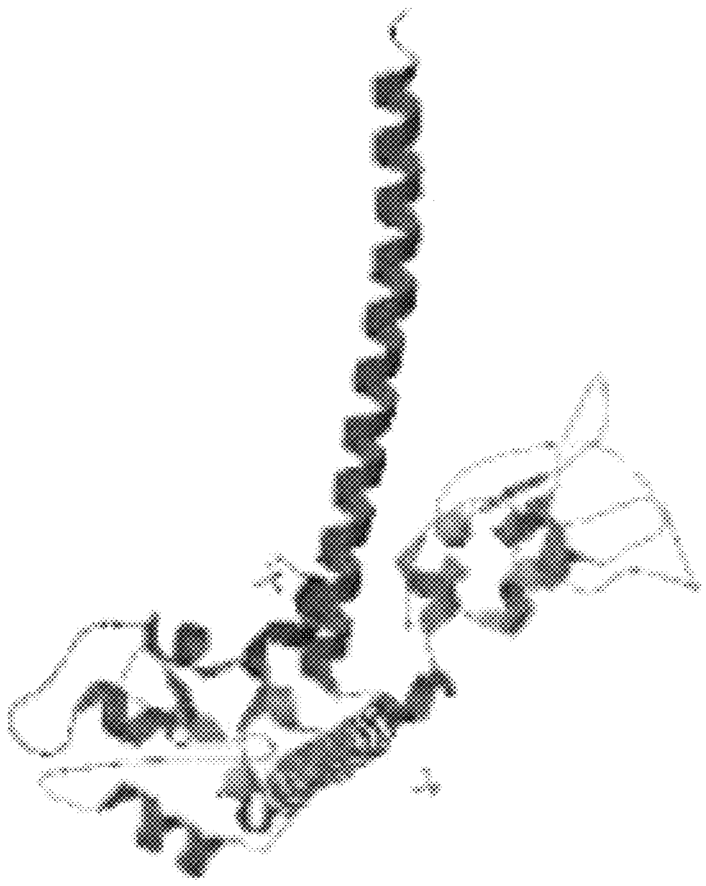
FIG. 4 is the schematic drawing showing the structure of survivin.
Figure 5:
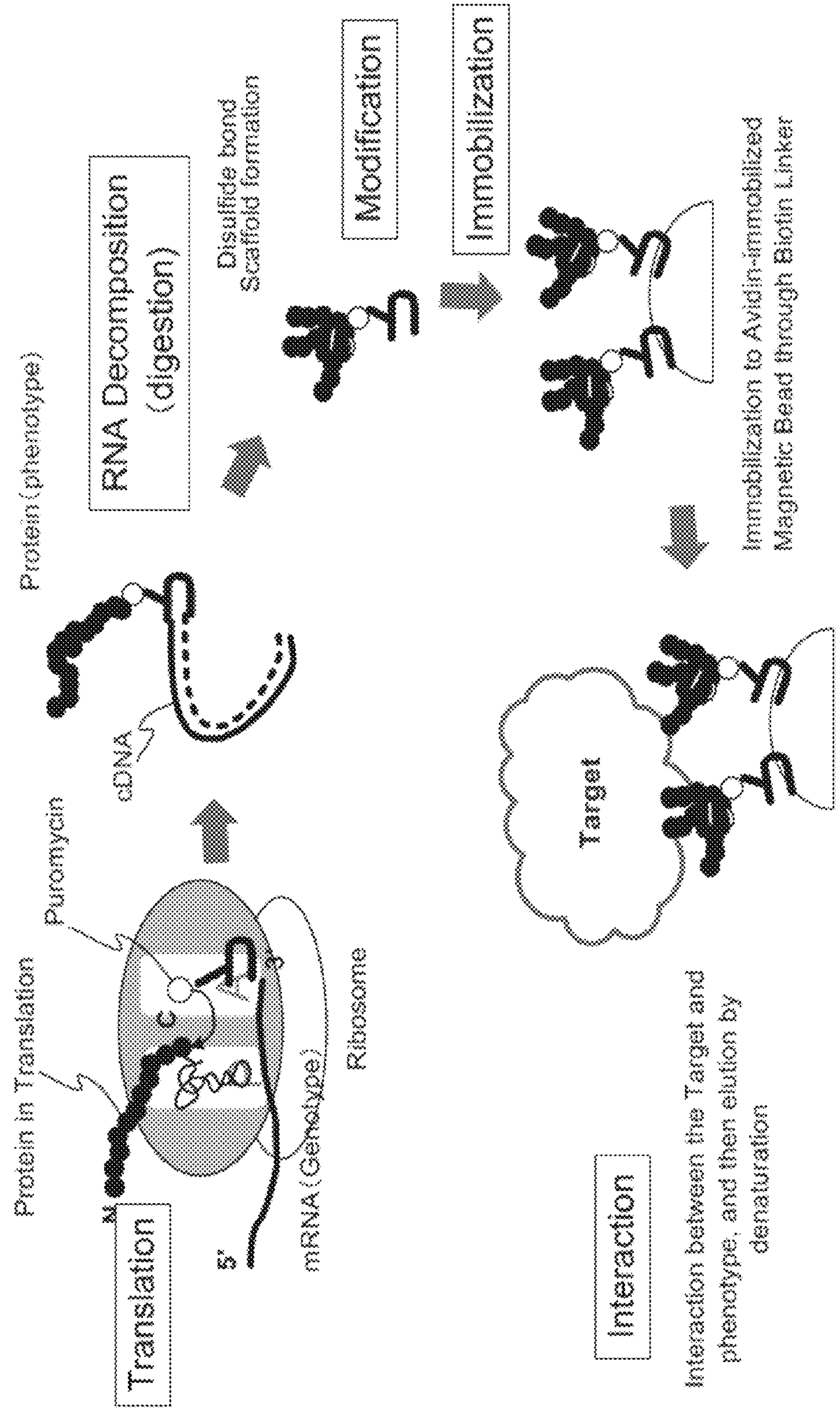
FIG. 5 is the schematic drawing when the linker to which the ligand of the present invention is bound is immobilized on the magnetic bead.

In FIG. 4, the structure of survivin is schematically shown. Survivin functions either monomer form or dimer form, however, they have complicated structures shown in FIG. 4. Also, survivin binds to the ligand of the present invention in which monomer or dimer form so that it is important as the disease marker. Also, the low molecular-weight compound is defined as those in the range of molecular weight of 30 to 1,500 with or without sugar chains. For example, there are mentioned such as aflatoxin B1, ciguatoxin, fluorescein, N-acetyl-D-glucosamine and the like. Particularly, aflatoxin B1, ciguatoxin and the like may be used, because of the prevention of food poisoning.

As the "randomized sequence", it may be selected from the following combination groups: X7 is anyone of those selected from the following group (A); X4 is anyone of those selected from the following group (B); and X2 is anyone of those selected from the following group (C); because the peptide having such randomized sequence is highly binding to the target molecule such as survivin, the low molecular-weight compound and the like.

(A) PTQPKRT (SEQ ID NO: 2), PNPADRN (SEQ ID NO: 4), NPPTSDT (SEQ ID NO: 6), PEVDIRQ (SEQ ID NO: 8), ETNNGQP (SEQ ID NO: 10), RRSMHTV (SEQ ID NO: 12) and PRTIRA (SEQ ID NO: 14).

(B) GTRQ (SEQ ID NO: 3), NPSH (SEQ ID NO: 5), PGNT (SEQ ID NO: 7), KLPR (SEQ ID NO: 9), TIPA (SEQ ID NO: 11), IAKN (SEQ ID NO: 13) and (SEQ ID NO: 15).

(C) PP, NR, TQ, KP, ER, TP and NQ.

Also, the combination of X7, X4 and X2 may be selected from the group consisting of (a) PTQPKRT (SEQ ID NO: 2), GTRQ (SEQ ID NO: 3), PP; (b) PNPADRN (SEQ ID NO: 4), NPSH (SEQ ID NO: 5), NR; (c) NPPTSDT (SEQ ID NO: 6), PGNT (SEQ ID NO: 7), TQ; (d) PEVDIRQ (SEQ ID NO: 8), KLPR (SEQ ID NO: 9), KP; (e) ETNNGQP (SEQ ID NO: 10), TIPA (SEQ ID NO: 11), ER; (f) RRSMHTV (SEQ ID NO: 12), IAKN (SEQ ID NO: 13), TP; (g) NPRTIRA (SEQ ID NO: 14), DLAE (SEQ ID NO: 15), NQ; because the peptide including them has higher binding ability to the target molecule as mentioned above.

Figure 6:
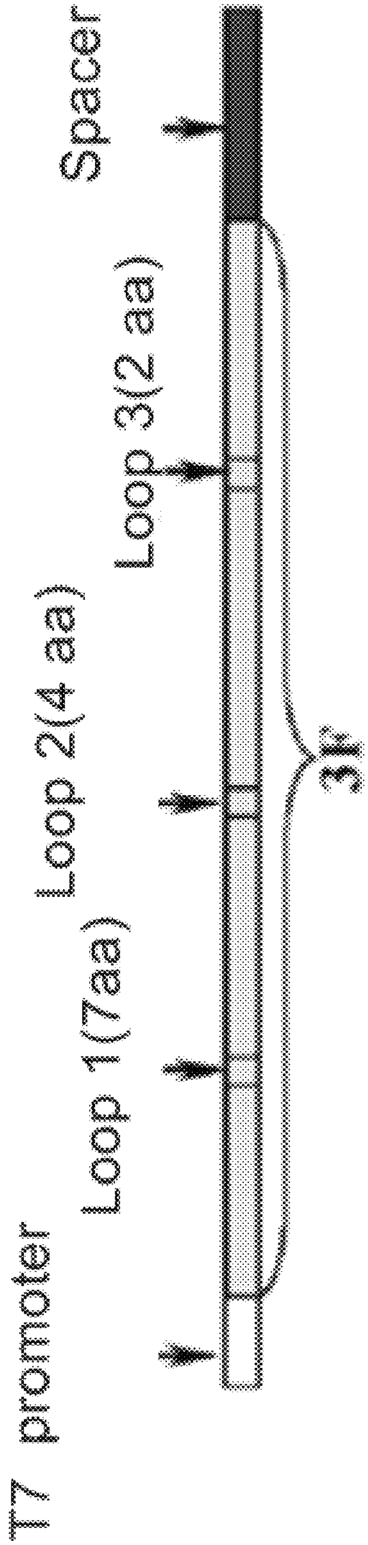
FIG. 6 is the schematic drawing showing the structure of the ligand of the present invention.
Figure 7:
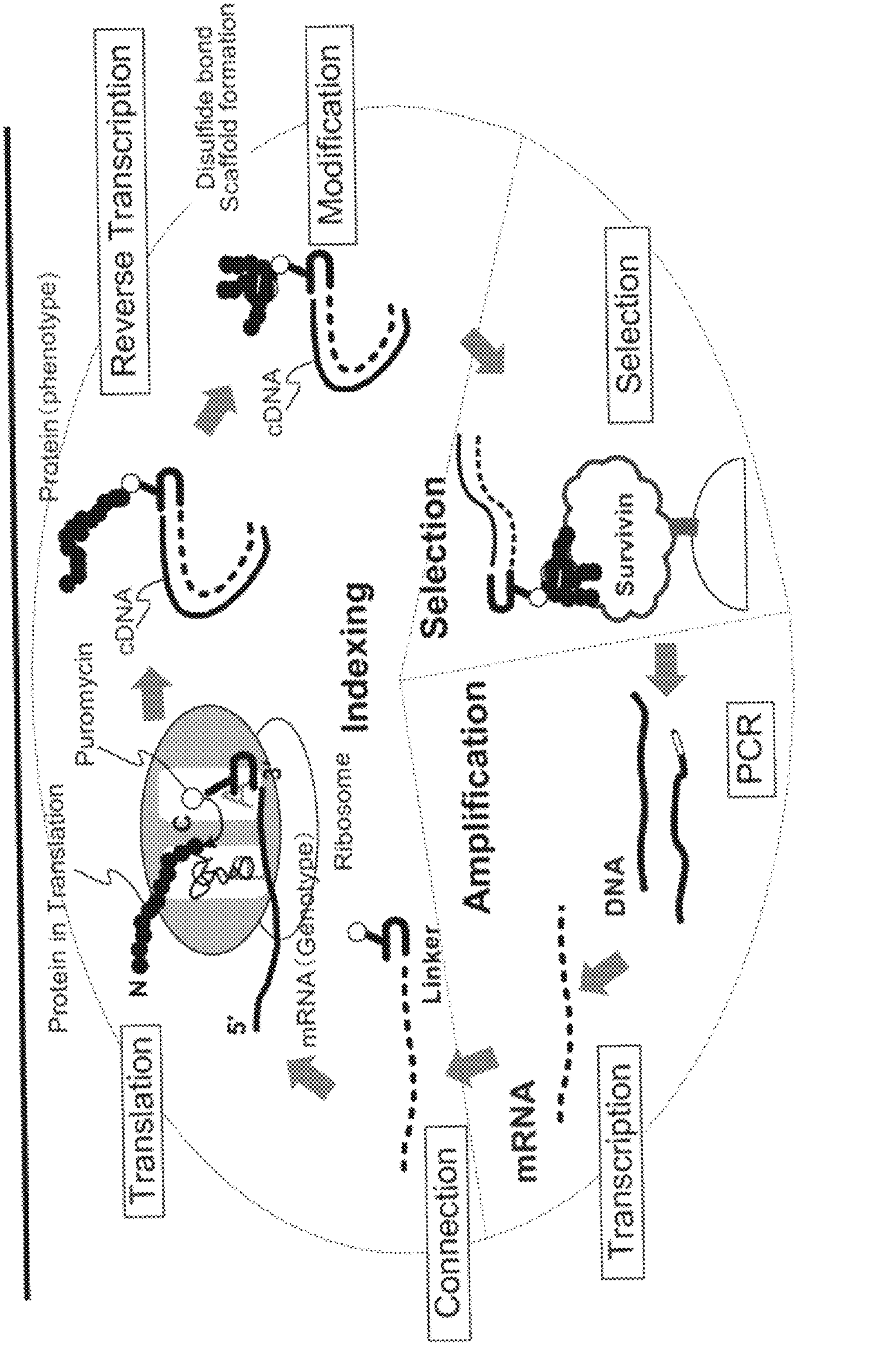
FIG. 7 is the schematic drawing showing the choice, amplification and selection of the ligand of the present invention by using IVV method.
Figure 8:
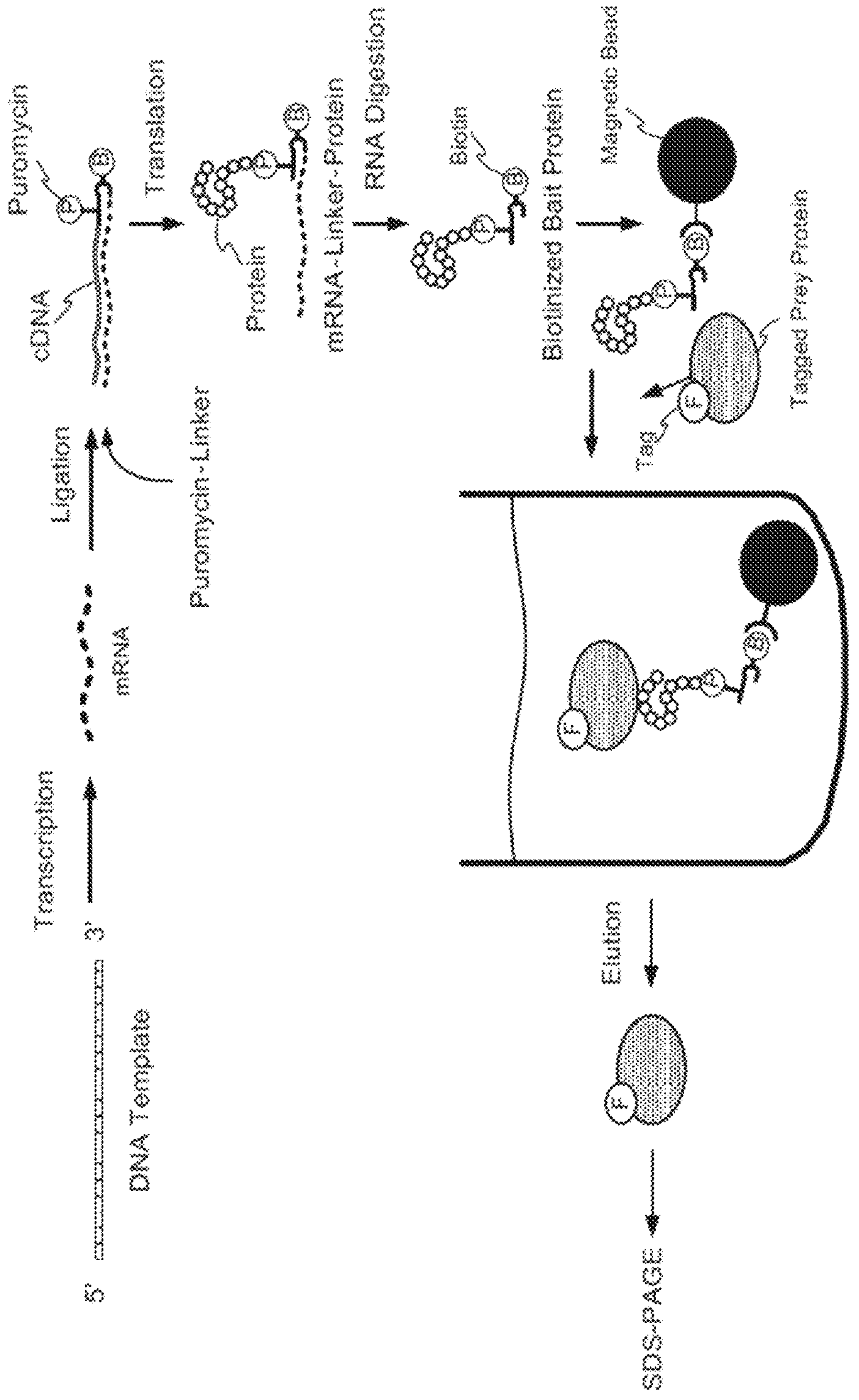
FIG. 8 is the schematic drawing showing the screening method of the present invention.

In FIG. 6, a DNA template including the above-mentioned randomized sequences therein is schematically shown. In FIG. 6, the terms, the "loop 1 (7aa)" means that the randomized sequence portion in the loop 1 is composed of the 7 amino acid as mentioned above. As the same as the loop 1, the loop 2 (4aa) and the loop 3 (2aa) mean that respective randomized sequence is composed of 4 and amino acids.

The combination of X6, X4 and X2 may be selected from the following groups: X6 is anyone of the sequence selected from the following group (A'); X4 is anyone of the sequence selected from the following group (B); and X2 is anyone of sequence selected from the following group (C), because the peptide including them has higher binding ability to the target molecule as mentioned above.

(A') the amino acid sequence composed of 6 amino acids by deletion of one amino acid among the following sequences, the SEQ ID NO: 2, SEQ ID NO: 4, SEQ ID NO: 6, SEQ ID NO: 8, SEQ ID NO: 10, RRSMHTV (SEQ ID NO: 12), and SEQ ID NO: 14, all of which are composed of 7 amino acids;

(B) GTRQ (SEQ ID NO: 3), NPSH (SEQ ID NO: 5), PGNT (SEQ ID NO: 7), KLPR (SEQ ID NO: 9), TIPA (SEQ ID NO: 11), IAKN (SEQ ID NO: 13) and DLAE (SEQ ID NO: 15);

(C) PP, NR, TQ, KP, ER, TP and NQ

The ligand of the present invention may exist as the form which is correlating to the polynucleotide coding to the ligand. It may bind to the polynucleotide coding the protein via puromycin. Because, the ligand having a variety of functions may be chosen effectively by existing the peptide as the correlating form as described above.

By using the ligand of the present invention, a variety of the disease marker may be detected. For example, the disease marker is detected through the steps of (a) preparing the above-mentioned ligand; (b) forming a ligand-target molecule conjugates by contacting the ligand with a serum to form; (c) choosing the ligand-target molecule conjugate; (d) measuring the chosen target molecular level in the sera.

The disease marker may be detected by using generally used UV detector, a detector using transmitted light to measure, the fluorescence detector and the like with desirable wave length. Among them, the fluorescence detection may be employed, because it is highly accurate.

In the present invention, the term, "cDNA display" is defined as the conjugate of the protein and the polynucleotide coding thereof, both of which are bound through puromycin, and includes mRNA-puromycin protein, cDNA/mRNA-puromycin proteins, and DNA-puromycin protein. Puromycin is a protein synthesis inhibitor having the structure similarly to that of the 3' terminal of amino acyl-tRNA, and it specifically binds to the 3' terminal of elongating protein on a ribosome under the predetermined conditions. When the mRNA and puromycin are bound via proper linker to synthesize the protein from the mRNA in a cell free system, the conjugate wherein the synthesized protein and mRNA coding it are bound via puromycin may be obtained (Nemoto et al., FEBS Lett., 414, 405-408, 1997).

Next, the protein having the desirable functions is chosen from the conjugate library. The conjugate of mRNA and the protein is reverse transcribed before the choice, or it is chosen as the mRNA/cDNA-protein conjugate. Also, by using the chosen conjugate, DNA may be synthesized after the choice. Namely, DNA is synthesized from the mRNA by using a reverse transcriptase to form the conjugate of mRNA/cDNA hybrid and the protein to choose it (Non patent document; Yamaguchi, et al., cDNA display: a novel screening method for functional disulfide-rich peptides by solid-phase synthesis and stabilization of mRNA-protein fusions, Nucleic Acids Res, 37, e108, 2009) (Non patent document; Mochizuki, et al., One-pot preparation of mRNA/cDNA display by a novel and versatile puromycin-linker DNA, ACS Comb. Sci., 13, 478-485, 2011).

The linker for ligand evolution used in the screening method of the present invention may be produced as follows.

The linker has the main chain comprising (a) a solid phase binding site (BB) having a predetermined molecule which forms the binding to BB; (b) a mRNA binding site (MB) located in the 5' terminal of the linker (main chain) to be recognized by RNA ligase; (c) a side chain binding site (SB) located closely to the 3' terminal of the linker (main chain), (d) a primer region (PR), located in the 3' terminal side of the linker (main chain), functions as a primer for the reverse transcription when the reverse transcription is performed on the linker; and (e) a side chain which is ligated to the side chain binding site (SB).

Here, the "solid phase" means the bead, side wall or inside bottom surface of a reaction container, to which the linker used in the present invention is directly or indirectly fixed. The magnetic bead may be employed, because it allows high throughput screening.

In the present specification, the term, "predetermined mRNA" comprises such as the mRNA of gene coding sequence, that necessary for forming the conjugate or promotion of the translation reaction, or that having other sequences and the like.

As the predetermined molecule used in (A), there are mentioned such as, for example, if avidin or streptavidin is immobilized on the solid phase, biotin; if the maltose binding protein is immobilized on the solid phase, maltose; if G protein is immobilized on the solid phase, guanine nucleotide; if polyhistidine peptide is bound to the solid phase, metals such as Ni or Co and the like; if glutathione-S-transferase is bound to the solid phase, glutathione; if the sequence specific protein is bound to the solid phase, sequence specific DNA or RNA for the protein; if the antibody or aptamer is bound to the solid phase, antigen or epitope; if calmodulin is bound to the solid phase, calmodulin binding protein; if ATP binding protein is bound to the solid phase, ATP; if estradiol receptor protein is bound to the solid phase, estradiol and the like.

Among them, biotin, maltose, metals such as Ni or Co, glutathione, antigen molecule, epitope peptide and the like may be used. Biotin may be used, because it leads easy synthesize of the linker. Such solid phase binding site (BB) is the site to which the above-mentioned mRNA-linker-protein conjugate is bound through the linker, and it may be composed of at least 10 bases. For example, it may be biotin modified deoxythimidine (dT) shown in the following formula (III).

[Chemical formula 1]

(III)

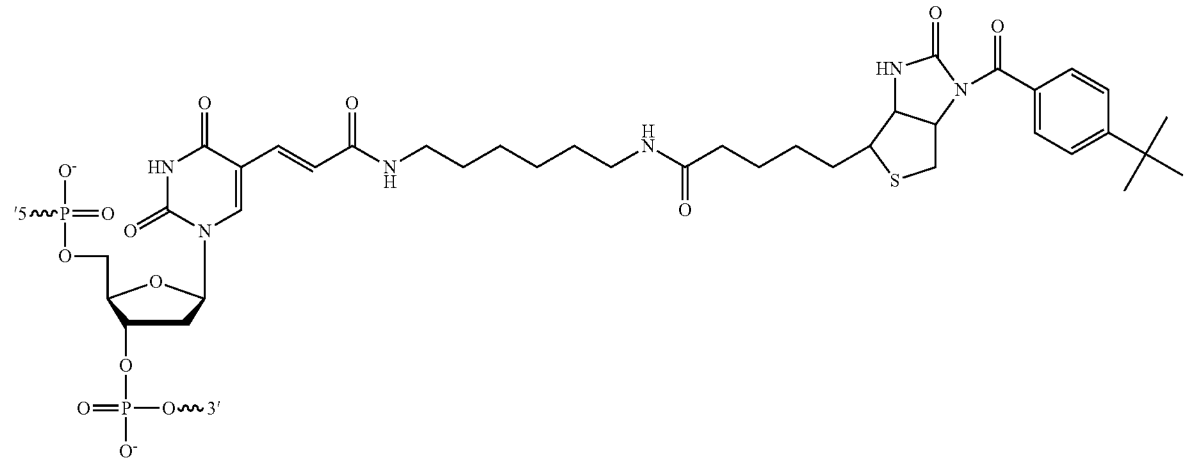

Introduction of particular polypeptides and the like to the solid phase binding site may be performed by using tannic acid, formalin, pyruvic aldehyde, glutaraldehyde, bisdiazotized benzidine, 2, 4-diisocyanate toluene. However, in order to avoid the denaturation of IVV, the affinity between molecules may be used.

The mRNA binding site may be composed of at least 1 to 10 bases. The mRNA binding site (MB) is not necessary to be previously phosphorylated. However, it should be phosphorylated by kinase and the like prior to the ligation to the 3' terminal of the mRNA or during the ligation reaction.

The side chain binding site (SB), located closely to the 3' terminal of the linker, is the binding side for the side chain as described below. Further, for example, when the side chain binding site (SB) is composed of Amino-Modifier C6 dT as shown in the following formula (IV), by replacing the 5' terminal of the side chain to 5'-Thiol-Modifier C6, the bridge between them are formed by using EMCS as shown in the following formula (VI) to bind the main chain and the side chain. Note that the following formula shows the EMCS with protecting groups.

[Chemical formula 2]

(IV)

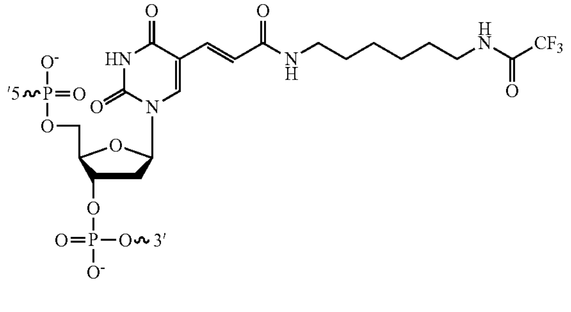

-continued

[Chemical formula 3]

(V)

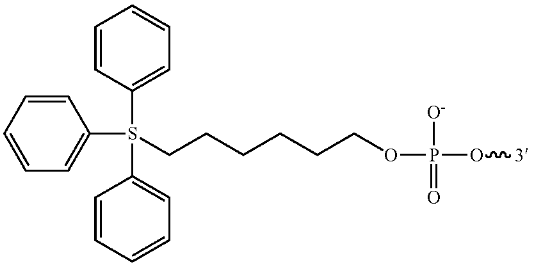

[Chemical formula 4]

(VI)

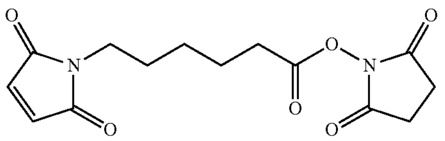

The primer region (PR) is located in the 3' terminal side of the linker, and it functions as the primer for the reverse transcription, when the reverse transcription is performed on the linker, adjacent to the 3' side of the side chain binding site.

Here, the primer region (PR) functions as the primer for the reverse transcription, when the reverse transcription is performed on the linker. It may be composed of 1 to 15 bases, especially composed of 3 to 5 bases. When the base number is more than 15, binding efficiency as the liker becomes poor. Therefore, the base number as mentioned above may be from the view points of the binding efficiency with the linker and the reaction efficiency as the primer.

The side chain which binds to the (f) side chain binding site comprises a spacer and a fluorescent group (F) between the protein binding site (P) which binds to the protein synthesized from the mRNA complementary to the main chain and the side chain binding site.

In so far as it has the function to specifically bind to the 3' terminal of the elongating protein except puromycin, optional puromycin derivatives may be used. For example, there are mentioned, for example, puromycin derivatives such as puromycin of which amino acid forms amido binding the 3' terminal of the nucleotide; ribocytidylic puromycin (rCpPur), deoxydylic puromycin (dCpPur), deoxyuridylic puromycin (dUpPur) and the like, 3'-N-aminoacyl puromycin amino nucleoside (PANS-amino acid), 3'-N-aminoacyl adenosine amino nucleoside (AANS-amino acid) and the like.

As PANS-amino acid, there are mentioned such as, for example, PANS-Gly, PANS-Val, PANS-Ala and the like. As AANS-amino acid, there are mentioned such as, for example, AANS-Gly, AANS-Val, AANS-Ala and the like. Alternatively, ester-linked nucleoside and the amino acid may be used. However, it may be employ puromycin, because the linkage of the protein at the protein binding site is highly stable.

A variety of derivative so as to design to include the modification to improve the stability of puromycin, the label for detecting the conjugate, affinity site for convenient purification, the binding site for convenient binding to other molecules and the like are commercially available, or they are conveniently produced. By employing the linker having the following structure, the disulfide bonding formation step may be introduced after the formation of mRNA/cDNA hybrid and the protein; as a result, three finger scaffold structure may be formed.

Also, as the spacer, the molecule may be used such as spacer 18 phosphoramidite shown in the following formula (VII), because they are flexible, and has low steric hindrance.

When the side chain is short, puromycin derivative is incorporated, the steric hindrance is generated. Therefore, the side chain may have the structure of a series of 1 to 8 of phosphoramidite molecule. From the view point of the balance between the efficiency of the linker synthesize and the formation of each conjugant as of 4 describe above, the structure of the conjugate of 4 molecules of the phosphoramidite molecules is preferable.

Since the side chain has the fluorescent group between the protein binding site and the side chain binding site, the presence or the absence of the linker can be conveniently detected in each step of cDNA display method described in below.

As the fluorescent group, it may be used, for example, the fluorescent compound having a carboxyl group being converted to active ester, a hydroxyl group being converted to phosphoramidite, or a free functional group such as amino group, and being ligated to the linker as the labelled base. As the fluorescent compound, there mentioned such as, for example, fluorescein isothiocyanate (FITC), phycobiliprotein, rare-earth metal chelate, dansyl chloride, tetramethyl rhodamine isothiocyanate, Fluorescein-dT and the like. Among them, Fluorescein-dT used as molecular labelling compound may be used, because it is readily synthesized. The chemical structural formula of Fluorescein-dT (VIII) is shown in below.

[Chemical formula 5]

(VII)

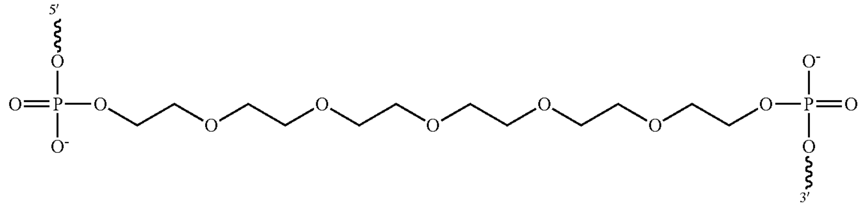

[Chemical formula 6]

(VIII)

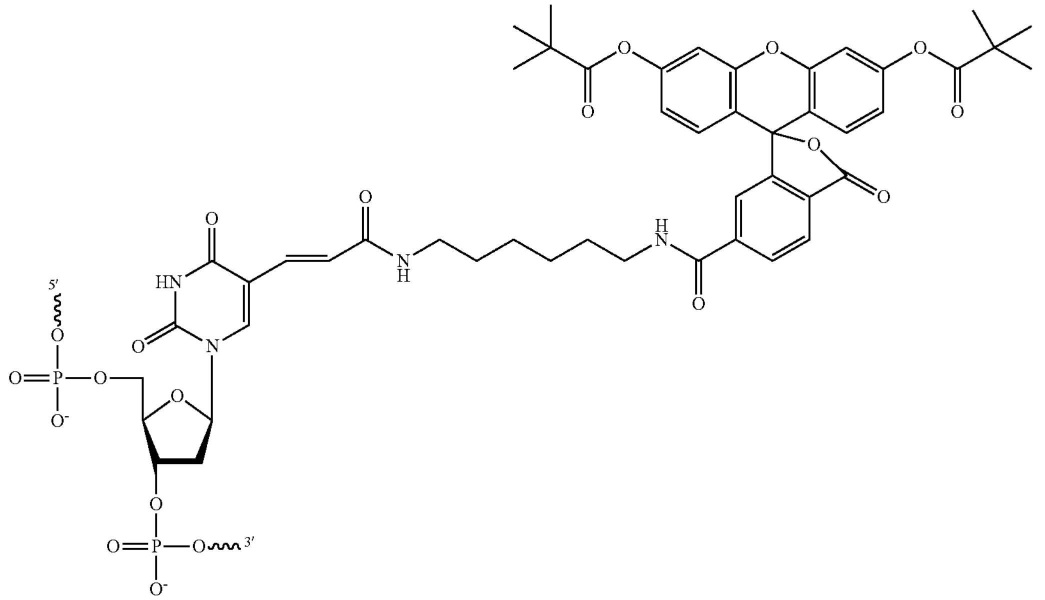

When the main chain is designed, the coding sequences of a variety of mRNA may be used as a reference. For example, there are mentioned mRNA such as that coding the sequences of variety receptor protein, having known coding sequence; that transcribed from DNA, having unknown sequences in a variety of gene library; that transcribed from randomly organic synthesized DNA, having a random sequence; that transcribed from DNA to which random mutation is introduced to code the protein having unknown sequence, and the like. As long as they do not include stop codon, they are chosen from those.

When the sequence does not include the stop codon, they incorporate 3' terminal analog of amino acyl tRNA such as puromycin, its derivative and the like at the C terminal of the polypeptide generated by the translation of the coding sequence of mRNA, thereby the polypeptide chain and mRNA-linker conjugate are ligated. Such mRNA may be obtained by using a variety of method such as in vitro transcription method, chemical synthesis, and extraction method from living body as a source, cells and microorganism. From the view point of the efficiencies of the ligation to the linker and cell free translation, they may be manufactured by using in vitro transcription method.

From the view point of the efficiency of the protein synthesis, they may have at least one of 7-methylguanosine 5' cap structure or 3' terminal poly A tail structure. They may have Kozak sequence or Shine-Dalgarno sequence for accelerating the start of the translation.

The length of mRNA used here is depending on that of coding region defined by the proteins or polypeptides to be evolved by using the present invention in principal. From the view point of reaction efficiency, the length may be in the range of 50 to 1,000 bases; it is preferably in the range of 200 to 500 bases, because the reaction efficiency becomes the highest.

In order to form the above-mentioned linker, firstly, DNA is synthesized by using the conventional method so as to be the predetermined sequence to prepare the single strand oligomer for use as the main chain. The oligomer synthesized as mentioned above comprises the solid phase binding site, the cleavage sites more than two, mRNA linkage site, the side chain binding site, and the primer region. The length of the single chain oligomer to become the main chain is properly decided on the basis of the size of two or more cleavage site and the positions in the main chain.

Next, the predetermined length of the side chain is synthesized to ligate on the side chain binding site of the main chain. The linker for the ligand evolution may be obtained by introducing, for example, puromycin to the free terminal of the side chain to introduce Fluorescein-dT described above into the fluorescent labelling site. The protein is identified by using the linker for the ligand evolution as described above to choose the protein having the predetermined functions to analyze DNA sequence.

Full length construct for three finger scaffold (herein below, it is sometimes called as "3F")-cDNA display including bucandin may be constructed by adding the fragment including the promoter at 5' side, cap site, untranslated sequence and translation start site, spacer at the 3' side, the tag, and the tag sequence. For example, the construct is manufactured as follows.

Figure 3:
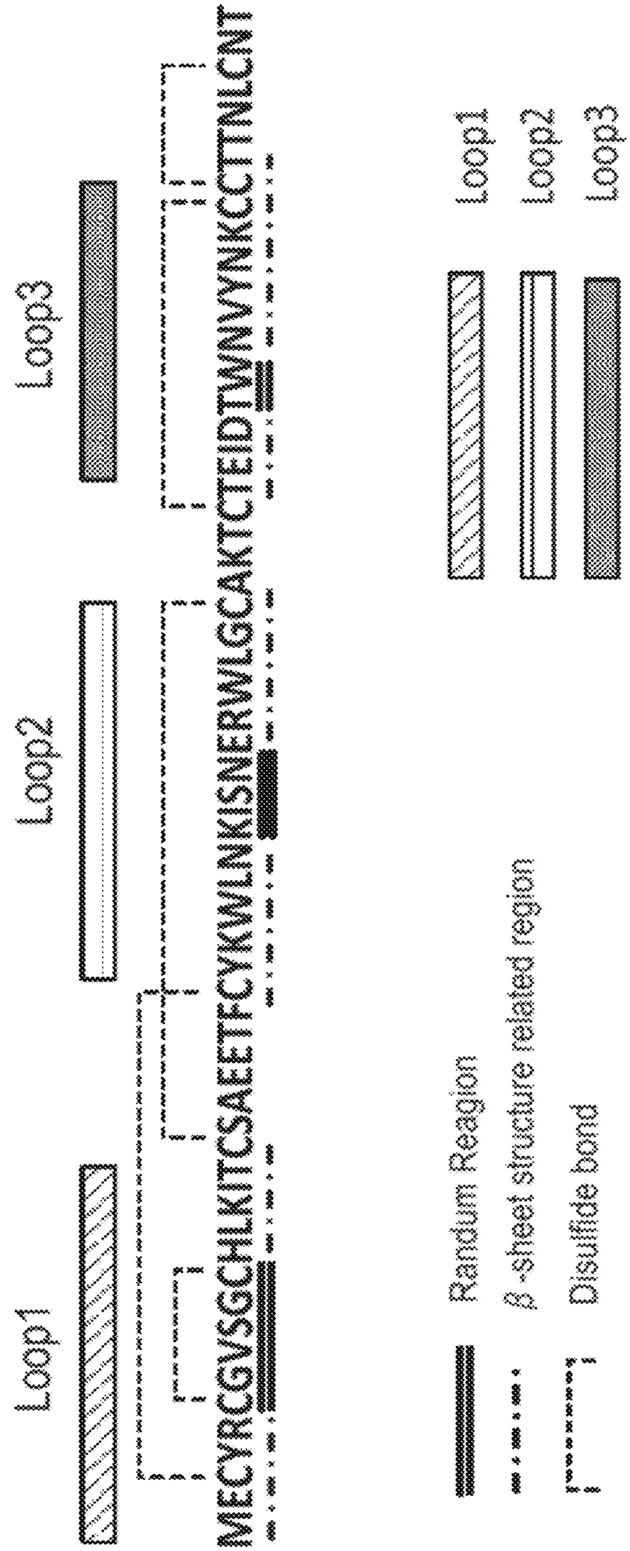
FIG. 3 is the drawing showing the structure of the present ligand as the amino acid sequence (SEQ ID NO: 58)

The amino acid sequence in each loop area is randomized, for example, at the position shown in FIG. 3. Next, the construct is designed to have T7-UTR fragment comprising T7 promoter, the cap site, ω sequence untranslated sequence (UTR), and the translation start site added to the 5' side of the base sequence of the modified ligand, and the spacer (GGGS (SEQ ID NO: 35)) 2, C-terminal His 6-tag (SEQ ID NO: 36), the spacer (GGGS (SEQ ID NO: 35)) and Y-tag sequence added to the 3' side of the base sequence (FIG. 6).

T7-UTR is used for the sequence for in vitro transcription and translation of the base sequence of the ligand of the present invention, His 6-tag (SEQ ID NO: 36) sequence is used for the library purification, Y-tag sequence is used for ligation of mRNA and puromycin linker. The spacer is introducing for smooth folding of the synthesized proteins.

The construct having the above-mentioned sequence is manufactured, and it is used in the cDNA display method as described above. Thereby, 3F scaffold in which X7, X4 and X2 parts described above are replaced by a variety of the sequence may be obtained. Namely, the translation is performed by using both of the predetermined amount of mRNA and the linker for ligand evolution under the predetermined conditions.

In the cell free translation system including little amount of dTT or nuclease content, for example, rabbit reticulocyte, a ribosome reads mRNA ligated to the linker to synthesize the protein, which is presented on puromycin. Next, mRNA is digested by RNase, and then the disulfide bonds are formed by using the cysteine contained in the protein to obtain the intended 3F scaffold. Then, by using the target molecule, for example, survivin, the 3F scaffold having the sequence shown in FIG. 3 is obtained.

In the interaction protein analysis by using the tagged protein, pull-down assay is the most popular one. In the pull-down assay, firstly, the target molecule and the tagged peptide are bound under the predetermined conditions to produce the tagged protein. Next, the tagged protein is mixed with the desirable protein extract to form the protein conjugate in vitro. The protein conjugate is reacted with the antibody, and then the reaction mixture is isolated by using centrifugation or the like. The obtained protein conjugate is separated by using SDS-PAGE to analyze fluorescence or the like (see FIG. 8).

For example, as the intended target protein, a small size protein, for example, survivin (see FIG. 4) is used. Survivin is bound to tagged peptide such as His-6 tag (SEQ ID NO: 36) and the like. Next, it is incubated, for example, 25° C. for 30 minutes, together with the 3F-cDNA display ligand obtained by the cDNA display method in the buffer including 100 mM NaCl, 50 mM Tris, 1 mM $CaCl_2$, pH 7.4.

Next, the desirable primer and the tagged sequence such as Y-tag sequence and the like are added to the buffer at the amount of 5 to 20 pmol, PCR amplification is performed at 20 to 30 cycles of the cycle, 90 to 98° C. for 15 to 30 second, 60 to 75° C. for 10 to 30 second, 67 to 80° C. for 15 to 45 second. At the same time, addition of the sequence used for the in vitro transcription and the translation of the obtained ligand, for example, T7-UTR, may be performed.

Y-tag sequence may be used for the ligation of mRNA and puromycin linker. Also, the incorporation of the spacer in the scaffold allows smooth folding of the synthesized protein. The scaffold is purified according to the conventional method to obtain the ligand for the detection of the disease marker as mentioned above. By adding the buffer to prepare the desirable concentration of the scaffold, the ligand solution for the reaction may be prepared. When the enough amount of the scaffold is formed, they may be used without particular purification.

For example, when the obtained sample is whole blood, it is centrifuged in the room temperature at low speed, for example, 1,000×g to separate serum. Then, the desirable amount of the serum is transferred into a reaction tube, and optionally diluted if desired. Then the ligand is added at the predetermined amount to the serum to form the ligand-target molecule conjugate. By binding the ligand to a molecular for the solid phase immobilization, the ligand is previously bound to the solid phase see FIG. 5). Then, the serum is eliminated to determine the target molecule level in the serum accurately and conveniently.

When the collected sample is a tissue fragment, it is homogenized according to the conventional method to isolate the supernatant. By treating the serum as the same as that as described above, the target molecular level in the tissue fragment may be accurately and conveniently.

According to the procedure as described above, the disease marker may be detected. By comparing the measurement value of the detected marker to the normal one, it is possible to assume whether the person is affected by the disease or not.

Here, the target molecule may be selected from the group consisting of survivin monomer, survivin dimer, and lower molecular weight compound; preferably survivin monomer or survivin dimer. The peptide aptamer may be used as the target molecule.

Also, the disease may be selected from the group consisting of tumors, infectious disease, and food poisoning. The tumor, infectious disease, and the food poisoning are as described above. Test in the early stage and start of early medical treatment may improve the effectiveness of the therapy.

As shown in FIG. 6, the screening method of the prey protein of the present invention comprises the steps of: (a) forming a mRNA-linker conjugate a linker for a ligand evolution and mRNA having complementary sequence by using RNA ligase at a mRNA binding site; (b) producing a linker-protein-mRNA conjugate wherein a protein having an enzyme activity is synthesized from cDNA synthesized by reverse transcription reaction with the mRNA as a template to obtain the linker-protein-mRNA conjugate on which the protein is bound at a protein binding site of the linker; (c) forming bait protein wherein mRNA is digested to obtain the bait protein which can be bound to a solid phase; (d) immobilizing the bait protein wherein a predetermined molecule bound to the solid phase binding site of the bait protein is ligated to the predetermined molecule immobilized on the solid phase; (e) reacting the bait protein and the labelled prey protein to generate a bait protein-prey protein conjugate; (f) collecting the bait protein-prey protein conjugate; and eluting the prey protein by washing the collected bait protein-prey protein conjugate.

Firstly, DNA template having the desirable sequence is prepared by using the conventional method. For example, the sequence comprising T7 promoter, omega sequence, Kozak sequence, bait protein coding region, and hybridization region (HR) of the puromycin linker. DNA describe above is transcribed by using T7 RiboMAX™ Express Large Scale RNA Production System (Promega) to mRNA, and then the synthesized mRNA is purified by using RNA purification kit (Qiagen).

Purified mRNA is ligated to puromycin linker by using T4 RNA ligase (Takarabaio Inc.) and polynucleotide kinase (hereinbelow, it sometimes abbreviated as "PNK", Toyobo); then the ligation product is used as the template of the in vitro translation reaction, for example, by using Retic Lysate IVT kit (Ambion) under the optional conditions to prepare mRNA-linker-protein fusant.

EDTA solution (0.5 M, pH 8.0) is added into the translation solution to delete the bound ribosome, and then RNase I (Promega) is added into the sample to decompose the mRNA part of mRNA-linker-bait protein fusant. Biotinylated bait protein as described above is caught from the solution by using Dynabeads MyOne Streptavidin C1 (Invitrogen), according to the manual provided by the manufacturer. IgG and anti-FLAG tagged mAb (mouse: purchased from Sigma-Aldrich), and anti-FasL mAb (hamster: Medical & Biological Laboratories) are prepared.

Each prey protein is labelled by using, for example, N-hydroxy succinimide (NHS)-fluorescein (Pierce). Then, obtained labelled prey protein solution is prepared at the predetermined concentration to incubate with the magnetic beads at the predetermined temperature at the predetermined temperature. For example, it is incubated with the protein solution prepared at the range of 100 to 500 nM at the temperature of 20 to 30 degree centigrade for 15 to 60 minutes.

Subsequently, the beads are washed several times with the phosphate buffered saline including the predetermined concentration of detergent to elute out the remained prey protein by using the solution for SDS-poly acrylamide gel electrophoresis (SDS-PAGE) sample. For example, they are washed with the phosphate buffered saline including 0.005 to 0.02% of TWEEN® 20 (PBS-T) 2 to 4 times. The protein being eluted by the SDS-PAGE sample solution is incubated at the predetermined temperature and time. For example, they are incubated at the temperature of 85 to 95 degree centigrade for 3 to 7 minutes; then the solution is subjected to Gel electrophoresis to visualize. As described above, the predetermined prey protein may be screened.

Hereinbelow, the present invention is explained more detail by using examples. However, the present invention is not limited to the examples.

EXAMPLES

(Example 1) Manufacture of the Ligand by Using Bucandin

Bucandin used in the present invention was purchased from Operon Biotechnology Inc. In order to manufacture the construct, T7-UTR fragment comprising T7-promoter, cap site, *Xenopus* globulin untranslated sequence (UTR) and translation start site, spacer (GGGS(SEQ ID NO: 35)) 2, His 6-tag (SEQ ID NO: 36), spacer (GGGS (SEQ ID NO: 35)) and Y-tag sequence were purchased from Geneworkd Inc.

Three loop areas of bucandin shown in FIG. 3 were respectively randomized by using the following method to obtain the set of amino acid sequence of No. 1 to 13 shown in the following Table 2.

TABLE 2

| | Loop Area (Replace amino acid number) | | | | | |
|---|---|---|---|---|---|---|
| No. | 1 (X7) | SEQ ID NO: | 2 (X4) | SEQ ID NO: | 3 (X2) | Round number |
| 1 | PTQPKRT | 2 | GTRQ | 3 | PP | 6 |
| 2 | NASAVRK | 37 | PETI | 38 | RG | 6 |
| 3 | IGEVSQR | 39 | EALK | 40 | GD | 6 |
| 4 | PNPADRN | 4 | NPSH | 5 | NR | 6 |
| 5 | TGLPPSD | 41 | PGAT | 42 | HN | 6 |
| 6 | TNMVNRP | 43 | PRRT | 44 | HR | 6 |
| 7 | NPPTSDT | 6 | PGNT | 7 | TQ | 6 |
| 8 | PTPIQGQ | 45 | NLPA | 46 | DA | 7 |
| 9 | QNEPLTA | 47 | NTTA | 48 | NG | 7 |
| 10 | PEVDIRQ | 8 | KLPR | 9 | KP | 12 |
| 11 | ETNNGQP | 10 | TIPA | 11 | ER | 12 |
| 12 | RRSMHTV | 12 | IAKN | 13 | TP | 12 |
| 13 | NPRTIRA | 14 | DLAE | 15 | NQ | 12 |

TABLE 2-continued

The 3F incorporating the amino acid sequence of No. 1 to 15 shown in Table 2, 3F (bucandin) loop 1, 3F (bucandin) loop 2, 3F (bucandin) loop 3 were ligated by using T4 DNA ligase, to which the T7-UTR fragment, His 6-tag (SEQ ID NO: 36) and the spacer were further ligated by using T4 DNA ligase. Then, by using T7-eXact-tagDNA, overlap PCR was performed for the conjugate to obtain the construct shown in FIG. 6.

(SEQ ID NO: 17)
5'-CTCAAAATAACGTGCTCGGCCGAGGAGACCTTCTGCTACA
AGTGGCTGAACAAG-3'

(SEQ ID NO: 18)
5'-CGTTGGCTGGGCTGCGCGAAGACTTGCACGGAGATCGACACC-3'.

Alternatively, as the primers, the following two synthesized oligomer were used.

(SEQ ID NO: 19)
5'-GATCCCGCGAAATTAATACGACTCACTATAGGG-3'

(SEQ ID NO: 20)
5'-TTTCCCCGCCGCCCCCCGTCCT-3'.

Furthermore, the sequence of the 3F (bucandin) loop 1 (88 mer) was as follows.

(SEQ ID NO: 21)
5'-TCCTCGGCCGAGCACGTTATTTTGAGNNBNNBNNBNNBNN
BNNBNNBGCGGTAGCACTCCATCAAAGCTTTGAAGAGCTT
GTCTTCTT-3'.

The sequence of the 3F (bucandin) loop 2 (60 mer) was as follows.

(SEQ ID NO: 22)
5'-TTCGCGCAGCCCAGCCAACGNNBNNBNNBNNBCTTGTTCA
GCCACTTGTAGCAGAAGGTC-3'.

Further, the sequence of the 3F (bucandin) loop 3 (113 mer) was as follows.

(SEQ ID NO: 23)
5'-TTTCCCCGCCGCCCCCCGTCCTTCCTGAGCCTCCACTCCC
TCCGCCCGTATTACATAGATTGGTAGTACAACATTTATTA
TATACNNBNNBGGTGTCGATCTCCGTGCAAGTC-3'.

The sequence of the T7-His-tagDNA was as follows.

```
                                          (SEQ ID NO: 24)
5'-GATCCCGCGAAATTAATACGACTCACTATAGGGGAAGTATTTTTACA
ACAATTACCAACAACAACAACAAACAACAACAACATTACATTTTACAT
TCTACAACTACAAGCCACCATGGGAGGGAAATCAAACGGGG-3'.
```

The obtained DNA was transcribed to mRNA by using T7 RiboMAX™ Express Large Scale RNA Production System (Promega); the synthesized mRNA was purified by using RNA purification kit (Qiagen).

(Example 2) IVV Assay (1) Synthesis of Puromycin-Biotin-Linker

Puromycin-biotin-linker for Puro-F-S (Geneworld) and biotin-loop (BEX Co, Ltd) were purchased. These two modified oligonucleotides were cross-linked by using bifunctional reagent (EMCS) according to the conventional method to synthesize Puromycin-biotin-linker. Puro-F-S used here was previously bound to puromycin at the one end of the spacer according to the conventional method and labelled with fluorescein. The Pyro-F-S had thiol group at another end.

Thiol group of 10 nmol of Puro-F-S was reduced by using to 100 μL of 50 mM phosphate buffer including 1 mM TCEP (tris (2-carboxyethyl) phosphine) (pH 7.0) for 6 hours at ambient temperature. Then, it was desalted just before use by using NAP-5 column (GE Healthcare). Both 10 nmol of biotin loop and 2 μmol of EMCS were added to 100 μL in total amount of sodium phosphate buffer (pH 7.0), and it was incubated at 37° C. for 30 minutes. Then, ethanol precipitation was performed at 4° C. to delete excess EMCS. The generated precipitation was washed with 500 μL of 70% ethanol previously cooled twice, and then it was dissolved in 10 μL of 0.2 M phosphate buffer (pH 7.0) previously cooled. Reduced Puro-F-S was quickly added and stirred at 4° C. overnight.

Reaction was stopped by adding 4 mM TCEP and incubated at 37° C. for 15 minutes. Next, ethanol precipitation was performed at ambient temperature to remove excess Puro-F-S. In order to remove the biotin loop and uncross-linked biotin loop-EMCS conjugate, 0.1 M TEAA (Glen Research Corp.) or 0.1 M phosphate buffer were added, and purified by using C18 HPLC under the following conditions.

Column: AR-300 (I.D. 4.6 mm×250 mm, Nacalai Tesque Inc.

Solvent A: 0.1 M TEAA

Solvent B: Acetonitrile/water (80/20, v/v)

Gradient: B/A (15-35%, 33 minutes)

Flow rate: 0.5 mL/minute

Detection: 254 nm and 490 nm

Fractions of last peak detected by 254 nm were collected. After drying them, the obtained puromycin linker was resuspended in diethyl pyrocarbonate (DEPC) treated water to store it. The biotin loop was composed of the base sequence to from stem loop structure and biotin bound to the loop moiety. In the stem moiety, the restriction site for the restriction enzyme PvuII was incorporated to recover IVV by cleaving the site. The 3' side sequence from the stem of the biotin loop was corresponding to Y-tag sequence in the full length construct as described above, and annealed the 3' side sequence of mRNA generated from the construct. In 5' terminal of it, the ligation with mRNA occurred.

The dT close to the 37 terminal of the biotin loop was modified so as to have a primary amino group. The biotin loop was bound to Puro-F-S via the amino acid by using EMCS. The 3' terminal of the biotin loop functioned as the primer, when the reverse transcription from the ligated mRNA was performed.

The thiol group of the puro-F-S was reduced, and the conjugate of the biotin loop and EMCS was added. The terminal thiol group of the Puro-F-S and the amino group were bound, and then the puromycin-biotin-linker was obtained.

(Example 3) Pull Down Assay (1) Binding of the Magnetic Beads

According to the instruction manual, the streptavidin coated magnetic beads (2.3 μm, MAGNOTEX, Takara Inc.) was washed twice with the binding buffer (10 mM Tris-HCl buffer containing 1 mM EDTA, 1 M NaCl, 0.1% Triton X-100 (pH 8.0)). 48 pmol of mRNA-puromycin linker conjugate and 1.2 mg of streptavidin beads were incubated in 120 μL of the binding buffer for 10 minutes at ambient temperature. Next, prior to add them to the cell free translation system, each bead was washed one by one by using both of the binding buffer and the translation mix buffer.

(2) Manufacture of the 3F-cDNA Display Ligand for Bait Protein Binding

After separation of the magnetic beads by using the magnetic stand, 300 μL of cell free translation extract (Ambion) was added, and incubated at 30° C. for 20 minutes. In order to increase yield of the protein-ligand fusant, the translation product was further incubated at 37° C. for 90 minutes under the hypertonic solution (KCl and $MgCl_2$, final concentrations were respectively 750 mM and 63 mM).

Then, the beads displaying mRNA-protein conjugate were washed twice by using 200 μL of the binding buffer including RNase inhibitor (SUPERaseIn, Ambion), and rinsed by using 100 μL of TR buffer including 50 mM Tris-HCl (pH 8.3, 75 mM KCl, 3 mM $MgCl_2$). The reverse transcription was performed at 42° C. for 10 minutes by adding 80 μL of RT buffer and 80 unit of reverse transcriptase M-MLV (Takara) to the beads. As described above, the cDNA-protein conjugate fixed magnetic beads, on the surface of the beads, cDNA-protein conjugate was bound, were obtained.

(3) Refolding

The cDNA-protein conjugate fixed magnetic beads obtained were reduced with 100 mM dithiothreitol (dTT) for 1 hour at 25° C.; and then washed by using the binding buffer (Takara). Refolding was performed 1 hour under the presence of 1 mM oxidized glutathione, 10 mM reduced glutathione, and equimolar protein disulfide isomerase with the used cDNA-protein conjugate. The beads were washed to obtain the bait protein fixed magnetic beads.

(4) Reaction with the Prey Protein

Next, each prey protein was labelled by using N-hydroxy succinimide (NHS)-fluorescein (Pierce) with the ratio of <1.0 label/protein. The obtained fluorescein-labelled prey protein solution (200 or 400 nM) was incubated with the bait protein fixed magnetic beads at 25° C. for 30 minutes. The beads were washed three times by using the phosphate buffered saline including 0.01% TWEEN® 20 (PBS-T). Next, the prey protein fixed on the magnetic beads was eluted by using the sample solution for SDS-polyacrylamide gel electrophoresis (SDS-PAGE).

PCR amplification and simultaneous addition of T7-UTR were performed by using 10 pmol of the eluted product, T7 sequence and the following primer including a part of UTR, (SEQ ID NO: 25)
[GATCCCGCGAAATTAATACGACTCACTATAGGGGAAGTATTTTTACAA

CAATTACCAACA];

and Y-tag sequence, respectively for 25 cycles of 95° C. for 25 second, 69° C. for 20 second, 72° C. for 30 second. The transcription was performed as the same as Example 2, and the obtained mRNA was ligated to puromycin to translate and then to reverse-transcribe to obtain DNA/mRNA-puromycin linker-protein conjugate.

The conjugate was used as the second 3F-cDNA display ligand in the next round. By repeating the procedure, choice was performed in plural rounds to manufacture the ligand. From the second round and subsequent rounds, the concentration of survivin as the target molecular was set at 200 pmol in the 1 to $4^{th}$ rounds, 100 pmol at $5^{th}$ round, 50 pmol at $6^{th}$ round, and reacted for the incubation time as 30 minutes.

At $7^{th}$ round, survivin concentration was set to 10 pmol and the incubation time was 15 minutes; at $8^{th}$ round, survivin concentration was 10 pmol and the incubation time was 5 minutes. From $9^{th}$ to $12^{th}$ rounds, survivin concentration was 10 pmol at $9^{th}$ round, 4 pmol at $10^{th}$ round, 1 pmol at $11^{th}$ round, 0.5 pmol at 12 round, and incubation time as 4 minutes in respective round. By increasing wash number, selection pressure was serially increased. Both survivin concentration in each round and incubation time were shown in Table 3.

TABLE 3

| Round No. | Survivin concentration (pM) | Incubation time (min.) |
|---|---|---|
| 1 | 200 | 30 |
| 2 | 200 | 30 |
| 3 | 200 | 30 |
| 4 | 200 | 30 |
| 5 | 100 | 30 |
| 6 | 50 | 30 |
| 7 | 10 | 15 |
| 8 | 10 | 5 |
| 9 | 10 | 4 |
| 10 | 4 | 4 |
| 11 | 1 | 4 |
| 12 | 0.5 | 4 |

Figure 9:
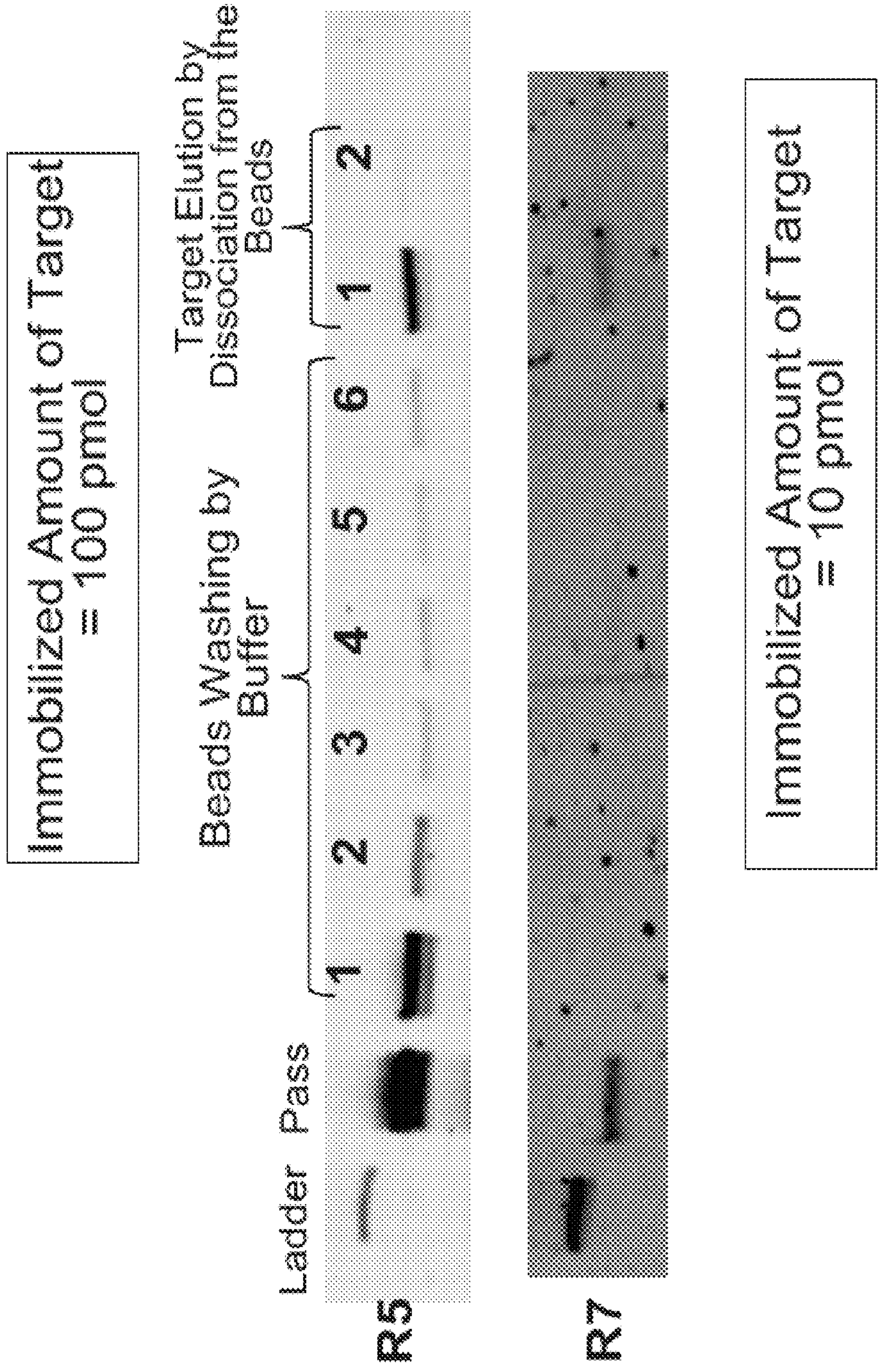
FIG. 9 is an image of gel electrophoresis showing status of the ligand and the target molecule obtained in the round 5 or round 7.

Clones in the $6^{th}$ round (R6) and $7^{th}$ round (R7), and 4 clones, 12 (A) to (D), in the $12^{th}$ round were obtained. In FIG. 9, comparison results of the $5^{th}$ round (R5) and $7^{th}$ round (R7) were shown. In FIG. 9, the result of beads washed by the buffer including 0.1 M NaCl, 50 mM Tris, and 1 mM $CaCl_2$, (pH 7.4), and that of eluted survivin by using EDTA to release from the beads were comparatively shown. Immobilized amount of survivin were 100 pmol in the R5, and 10 pmol at the R7.

As shown in FIG. 9, in the R5, low binding ability was eluted by washing, but in the R7, such elution was not observed. On the other hand, the same results were obtained in each round in two lanes to which eluents of survivin released from the beads were applied. As a result, it was shown that the binding ability of the ligand increased with rounds.

Next, the ligands obtained in the round $6^{th}$, $7^{th}$ and $12^{th}$ were fixed on the streptavidin induced Sepharose beads (the magnetic beads) by using puromycin-biotin linker to bind survivin with fluorescent modification. The beads were washed by using the buffer including Tris-HCl (pH 8.0), 100 mM, 150 mM NaCl, 1 mM EDTA, 0.1% TWEEN® 20, and 10 μM biotin, and then 25 μL of SDS-PAGE sample buffer including 0.5 M Tris-HCl, 10% SDS, 10% β-mercaptoethanol, 175 mM sucrose, and 8 M urea was used to elute survivin. 12 μL of each eluents were subjected to 4%+16% SD S-PAGE, and electrophoresed at 10 mA for 130 minutes to detect the results with FITC. The results were shown in FIG. 9. According to the electrophoresis of the round 6 and 7, it was decided that the amounts of survivin eluted at No. 1, 4, 7 and 10 were much (see FIG. 10).

The binding abilities of 4 ligands obtained in the round 12 (R12A to R12D) were compared to those obtained in the $6^{th}$ round (R6) and the $7^{th}$ round (R7). Results were shown in FIG. 11. The results of the gel electrophoresis were shown in the upper column of FIG. 11, and the binding abilities based on the amounts of eluted survivin were shown in the lower column. The ligands, B to D of the round 12 had high binding ability compared to those of the round 6 and 7, particularly, R12B had high binding ability.

Accordingly, it was confirmed that the ligand which enable to recognize survivin was manufactured by using cDNA display method; and the ligand having high binding ability was chosen under the increased selection pressure.

One of the advantages of the present invention is that it contributes to the technique to detect the novel protein or the polypeptide, and it is useful in the pharmaceutical or diagnosis agents.

Sequence Listing Free Text

SEQ ID NO: 1: Three finger protein having protruded disulfide bonds, β-sheet and three protruded loop; Xaa is an arbitrary amino acid;

SEQ ID NO: 2: A part inside loop 1 of the three finger protein;

SEQ ID NO: 3: A part inside loop 2 of the three finger protein;

SEQ ID NO: 4: A part inside loop 1 of the three finger protein;

SEQ ID NO: 5: A part inside loop 2 of the three finger protein;

SEQ ID NO: 6: A part inside loop 1 of the three finger protein;

SEQ ID NO: 7: A part inside loop 2 of the three finger protein;

SEQ ID NO: 8: A part inside loop 1 of the three finger protein;

SEQ ID NO: 9: A part inside loop 2 of the three finger protein;

SEQ ID NO: 10: A part inside loop 1 of the three finger protein;

SEQ ID NO: 11: A part inside loop 2 of the three finger protein;

SEQ ID NO: 12: A part inside loop 1 of the three finger protein;

SEQ ID NO: 13: A part inside loop 2 of the three finger protein;

SEQ ID NO: 14: A part inside loop 1 of the three finger protein;

SEQ ID NO: 15: A part inside loop 2 of the three finger protein;

SEQ ID NO: 16: Three finger protein having the protruded disulfide bonds, the β-sheet and three protruded loop; Xaa is an arbitrary amino acid;

SEQ ID NO: 17: Splint DNA;

SEQ ID NO: 18: Splint DNA;

SEQ ID NO: 19: A primer for manufacturing a three finger protein-cDNA conjugate;

SEQ ID NO: 20: A primer for manufacturing the three finger protein-cDNA conjugate;

SEQ ID NO: 21: 3F (bucandin) loop1; n is an arbitrary nucleotide;

SEQ ID NO: 22: 3F (bucandin) loop2; n is an arbitrary nucleotide;

SEQ ID NO: 23: 3F (bucandin) loop3; n is an arbitrary nucleotide;

SEQ ID NO: 24: T7-eXact-tagDNA;

SEQ ID NO: 25: A primer for concentrating the three finger protein-cDNA conjugate.

---

The invention claimed is:

1. A ligand having three fingers, wherein each finger comprises anti-parallel β-sheets and a loop area sandwiched between them, wherein the loop area forms a fingertip, wherein the ligand binds to a target molecule through the fingertip, and wherein the ligand comprises the amino acid sequence (SEQ ID NO: 1)
MECYR(X7)LKITCSAEETFCYKWLNK(X4)RWLGCAKTCTEID(X2)N
VYNKCCTTNLCNT, wherein X7 consists of 7 amino acids selected from the group consisting of PTQPKRT (SEQ ID NO: 2), PNPADRN (SEQ ID NO: 4), NPPTSDT (SEQ ID NO: 6), PEVDIRQ (SEQ ID NO: 8), ETNNGQP (SEQ ID NO: 10), RRSMHTV (SEQ ID NO: 12) and NPRTIRA (SEQ ID NO: 14), X4 consists of 4 amino acids selected from the group consisting of GTRQ (SEQ ID NO: 3), NPSH (SEQ ID NO: 5), PGNT (SEQ ID NO: 7), KLPR (SEQ ID NO: 9), TIPA (SEQ ID NO: 11), IAKN (SEQ ID NO: 13) and DLAE (SEQ ID NO: 15), and X2 consists of 2 amino acids selected from the group consisting of PP, NR, TQ, KP, ER, TP and NQ.

2. The ligand according to claim 1, wherein the ligand comprises an amino acid sequence selected from the group consisting of SEQ ID NOs: 50-56.

3. The ligand according to claim 1, wherein the target molecule is selected from the group consisting of survivin monomer, survivin dimer and low molecular-weight compound.

4. The ligand according to claim 1, wherein the ligand binds to a polynucleotide encoding the ligand.

5. The ligand according to claim 1, wherein the ligand binds to a polynucleotide encoding the ligand through puromycin.

6. A ligand having three fingers, wherein each finger comprises anti-parallel β sheets and a loop area sandwiched between them, wherein the loop area forms a fingertip, wherein the ligand binds to a target molecule through the fingertip, and wherein the ligand comprises the amino acid sequence:

(SEQ ID NO: 16)
MECYR(X6)LKITCSAEETFCYKWLNK(X4)RWLGCAKTCTEID(X2)
NVYNKCCTTNLCNT wherein X6 is 6 amino acids in length and consists of an amino acid sequence selected from the group consisting of PTQPKRT (SEQ ID NO: 2), PNPADRN (SEQ ID NO: 4), NPPTSDT (SEQ ID NO: 6), PEVDIRQ (SEQ ID NO: 8), ETNNGQP (SEQ ID NO: 10), RRSMHTV (SEQ ID NO:12), and NPRTIRA (SEQ ID NO: 14), wherein one amino acid is deleted from the amino acid sequences of SEQ ID NOs: 2, 4, 6, 8, 10, 12 or 14;

wherein X4 consists of 4 amino acids and is GTRQ (SEQ ID NO: 3), NPSH (SEQ ID NO: 5), PGNT (SEQ ID NO: 7), KLPR (SEQ ID NO: 9), TIPA (SEQ ID NO: 11), IAKN (SEQ ID NO: 13), or DLAE (SEQ ID NO: 15); and wherein X2 is PP, NR, TQ, KP, ER, TP or NQ.

7. The ligand according to claim 6, wherein the target molecule is selected from the group consisting of survivin monomer, survivin dimer, and low molecular-weight compound.

8. The ligand according to claim 6, wherein the ligand binds to a polynucleotide encoding the ligand.

9. The ligand according to claim 6, wherein the ligand binds to a polynucleotide via puromycin.

10. A ligand having three fingers, wherein each finger comprises anti-parallel β-sheets and a loop area sandwiched between them, wherein the loop area forms a fingertip, wherein the ligand binds to a target molecule through the fingertip, and wherein the ligand comprises the amino acid sequence (SEQ ID NO: 1)
MECYR(X7)LKITCSAEETFCYKWLNK(X4)RWLGCAKTCTEID(X2)N
VYNKCCTTNLCNT, and wherein X represents any amino acid except cysteine, X7 consists of 7 amino acids, X4 consists of 4 amino acids, and the total number of cysteine residues in SEQ ID NO: 1 is 8.

11. The ligand according to claim 10, wherein X7 does not consist of 7 identical amino acids, and wherein X4 does not consist of 4 identical amino acids.

* * * * *

SEQUENCE LISTING

```
<160> NUMBER OF SEQ ID NOS: 58

<210> SEQ ID NO 1
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(12)
<223> OTHER INFORMATION: Any amino acid
<220> FEATURE:
<221> NAME/KEY: MOD_RES
<222> LOCATION: (31)..(34)
<223> OTHER INFORMATION: Any amino acid
<220> FEATURE:
<221> NAME/KEY: MOD_RES
<222> LOCATION: (48)..(49)
<223> OTHER INFORMATION: Any amino acid
<220> FEATURE:
<223> OTHER INFORMATION: See specification as filed for detailed
      description of substitutions and preferred embodiments

<400> SEQUENCE: 1

Met Glu Cys Tyr Arg Xaa Xaa Xaa Xaa Xaa Xaa Xaa Leu Lys Ile Thr
1               5                   10                  15

Cys Ser Ala Glu Glu Thr Phe Cys Tyr Lys Trp Leu Asn Lys Xaa Xaa
            20                  25                  30

Xaa Xaa Arg Trp Leu Gly Cys Ala Lys Thr Cys Thr Glu Ile Asp Xaa
        35                  40                  45

Xaa Asn Val Tyr Asn Lys Cys Cys Thr Thr Asn Leu Cys Asn Thr
    50                  55                  60


<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Thr Gln Pro Lys Arg Thr
1               5


<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Thr Arg Gln
1


<210> SEQ ID NO 4
```

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Pro Asn Pro Ala Asp Arg Asn
1 5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Asn Pro Ser His
1

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Asn Pro Pro Thr Ser Asp Thr
1 5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Pro Gly Asn Thr
1

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Pro Glu Val Asp Ile Arg Gln
1 5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

-continued

Lys Leu Pro Arg
1

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Glu Thr Asn Asn Gly Gln Pro
1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Thr Ile Pro Ala
1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Arg Arg Ser Met His Thr Val
1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Ile Ala Lys Asn
1

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Asn Pro Arg Thr Ile Arg Ala
1               5

<210> SEQ ID NO 15
<211> LENGTH: 4
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 15

Asp Leu Ala Glu
1

<210> SEQ ID NO 16
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(11)
<223> OTHER INFORMATION: Any amino acid
<220> FEATURE:
<221> NAME/KEY: MOD_RES
<222> LOCATION: (30)..(33)
<223> OTHER INFORMATION: Any amino acid
<220> FEATURE:
<221> NAME/KEY: MOD_RES
<222> LOCATION: (47)..(48)
<223> OTHER INFORMATION: Any amino acid

<400> SEQUENCE: 16

Met Glu Cys Tyr Arg Xaa Xaa Xaa Xaa Xaa Xaa Leu Lys Ile Thr Cys
1               5                   10                  15

Ser Ala Glu Glu Thr Phe Cys Tyr Lys Trp Leu Asn Lys Xaa Xaa Xaa
            20                  25                  30

Xaa Arg Trp Leu Gly Cys Ala Lys Thr Cys Thr Glu Ile Asp Xaa Xaa
        35                  40                  45

Asn Val Tyr Asn Lys Cys Cys Thr Thr Asn Leu Cys Asn Thr
    50                  55                  60

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctcaaaataa cgtgctcggc cgaggagacc ttctgctaca agtggctgaa caag           54

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgttggctgg gctgcgcgaa gacttgcacg gagatcgaca cc                        42

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gatcccgcga aattaatacg actcactata ggg 33

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
tttccccgcc gccccccgtc ct 22

<210> SEQ ID NO 21
<211> LENGTH: 88
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: modified_base
<222> LOCATION: (33)..(34)
<223> OTHER INFORMATION: a, c, t, g, unknown or other
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: modified_base
<222> LOCATION: (42)..(43)
<223> OTHER INFORMATION: a, c, t, g, unknown or other
<220> FEATURE:
<221> NAME/KEY: modified_base
<222> LOCATION: (45)..(46)
<223> OTHER INFORMATION: a, c, t, g, unknown or other

<400> SEQUENCE: 21
tcctcggccg agcacgttat tttgagnnbn nbnnbnnbnn bnnbnnbgcg gtagcactcc 60
atcaaagctt tgaagagctt gtcttctt 88

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (21)..(22)
<223> OTHER INFORMATION: a, c, t, g, unknown or other
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other

<400> SEQUENCE: 22
ttcgcgcagc ccagccaacg nnbnnbnnbn nbcttgttca gccacttgta gcagaaggtc 60

<210> SEQ ID NO 23
<211> LENGTH: 113
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (86)..(87)
<223> OTHER INFORMATION: a, c, t, g, unknown or other
<220> FEATURE:
<221> NAME/KEY: modified_base
<222> LOCATION: (89)..(90)
<223> OTHER INFORMATION: a, c, t, g, unknown or other

<400> SEQUENCE: 23
tttccccgcc gccccccgtc cttcctgagc ctccactccc tccgcccgta ttacatagat 60
tggtagtaca acatttatta tatacnnbnn bggtgtcgat ctccgtgcaa gtc 113

<210> SEQ ID NO 24
<211> LENGTH: 136
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24
gatcccgcga aattaatacg actcactata ggggaagtat ttttacaaca attaccaaca 60
acaacaacaa acaacaacaa cattacattt tacattctac aactacaagc caccatggga 120
gggaaatcaa acgggg 136

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gatcccgcga aattaatacg actcactata ggggaagtat ttttacaaca attaccaaca 60

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Gly Val Ser Gly Cys His
1 5

<210> SEQ ID NO 27
<211> LENGTH: 4

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Ile Ser Asn Glu
1

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Thr Gln Pro Lys Arg Thr
1 5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Pro Gln Pro Lys Arg Thr
1 5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Pro Thr Pro Lys Arg Thr
1 5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Pro Thr Gln Lys Arg Thr
1 5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Pro Thr Gln Pro Arg Thr

-continued

```
1               5


<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Thr Gln Pro Lys Thr
1               5


<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Thr Gln Pro Lys Arg
1               5


<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Ser
1


<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 36

His His His His His His
1               5


<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asn Ala Ser Ala Val Arg Lys
1               5


<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 38

Pro Glu Thr Ile
1

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Ile Gly Glu Val Ser Gln Arg
1 5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Glu Ala Leu Lys
1

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Thr Gly Leu Pro Pro Ser Asp
1 5

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Pro Gly Ala Thr
1

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Thr Asn Met Val Asn Arg Pro
1 5

<210> SEQ ID NO 44

<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Pro Arg Arg Thr
1

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Pro Thr Pro Ile Gln Gly Gln
1 5

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Asn Leu Pro Ala
1

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Gln Asn Glu Pro Leu Thr Ala
1 5

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Asn Thr Thr Ala
1

<210> SEQ ID NO 49
<211> LENGTH: 63
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (6)..(12)

```
<223> OTHER INFORMATION: This region may encompass 'PTQPKRT', 'PNPADRN',
      'NPPTSDT', 'PEVDIRQ', 'ETNNGQP', 'RRSMHTV' or 'NPRTIRA'
<220> FEATURE:
<221> NAME/KEY: MOD_RES
<222> LOCATION: (31)..(34)
<223> OTHER INFORMATION: This region may encompass 'GTRQ', 'NPSH',
      'PGNT', 'KLPR', 'TIPA', 'IAKN' or 'DLAE'
<220> FEATURE:
<221> NAME/KEY: MOD_RES
<222> LOCATION: (48)..(49)
<223> OTHER INFORMATION: This region may encompass 'PP', 'NR', 'TQ',
      'KP', 'ER', 'TP' or 'NQ'
<220> FEATURE:
<223> OTHER INFORMATION: See specification as filed for detailed
      description of substitutions and preferred embodiments

<400> SEQUENCE: 49

Met Glu Cys Tyr Arg Xaa Xaa Xaa Xaa Xaa Xaa Xaa Leu Lys Ile Thr
1               5                   10                  15

Cys Ser Ala Glu Glu Thr Phe Cys Tyr Lys Trp Leu Asn Lys Xaa Xaa
            20                  25                  30

Xaa Xaa Arg Trp Leu Gly Cys Ala Lys Thr Cys Thr Glu Ile Asp Xaa
        35                  40                  45

Xaa Asn Val Tyr Asn Lys Cys Cys Thr Thr Asn Leu Cys Asn Thr
    50                  55                  60


<210> SEQ ID NO 50
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Glu Cys Tyr Arg Pro Thr Gln Pro Lys Arg Thr Leu Lys Ile Thr
1               5                   10                  15

Cys Ser Ala Glu Glu Thr Phe Cys Tyr Lys Trp Leu Asn Lys Gly Thr
            20                  25                  30

Arg Gln Arg Trp Leu Gly Cys Ala Lys Thr Cys Thr Glu Ile Asp Pro
        35                  40                  45

Pro Asn Val Tyr Asn Lys Cys Cys Thr Thr Asn Leu Cys Asn Thr
    50                  55                  60


<210> SEQ ID NO 51
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Glu Cys Tyr Arg Pro Asn Pro Ala Asp Arg Asn Leu Lys Ile Thr
1               5                   10                  15

Cys Ser Ala Glu Glu Thr Phe Cys Tyr Lys Trp Leu Asn Lys Asn Pro
            20                  25                  30

Ser His Arg Trp Leu Gly Cys Ala Lys Thr Cys Thr Glu Ile Asp Asn
        35                  40                  45

Arg Asn Val Tyr Asn Lys Cys Cys Thr Thr Asn Leu Cys Asn Thr
    50                  55                  60


<210> SEQ ID NO 52
<211> LENGTH: 63
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

Met Glu Cys Tyr Arg Asn Pro Pro Thr Ser Asp Thr Leu Lys Ile Thr
1 5 10 15

Cys Ser Ala Glu Glu Thr Phe Cys Tyr Lys Trp Leu Asn Lys Pro Gly
20 25 30

Asn Thr Arg Trp Leu Gly Cys Ala Lys Thr Cys Thr Glu Ile Asp Thr
35 40 45

Gln Asn Val Tyr Asn Lys Cys Cys Thr Thr Asn Leu Cys Asn Thr
50 55 60

<210> SEQ ID NO 53
<211> LENGTH: 63
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Met Glu Cys Tyr Arg Pro Glu Val Asp Ile Arg Gln Leu Lys Ile Thr
1 5 10 15

Cys Ser Ala Glu Glu Thr Phe Cys Tyr Lys Trp Leu Asn Lys Lys Leu
20 25 30

Pro Arg Arg Trp Leu Gly Cys Ala Lys Thr Cys Thr Glu Ile Asp Lys
35 40 45

Pro Asn Val Tyr Asn Lys Cys Cys Thr Thr Asn Leu Cys Asn Thr
50 55 60

<210> SEQ ID NO 54
<211> LENGTH: 63
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 54

Met Glu Cys Tyr Arg Glu Thr Asn Asn Gly Gln Pro Leu Lys Ile Thr
1 5 10 15

Cys Ser Ala Glu Glu Thr Phe Cys Tyr Lys Trp Leu Asn Lys Thr Ile
20 25 30

Pro Ala Arg Trp Leu Gly Cys Ala Lys Thr Cys Thr Glu Ile Asp Glu
35 40 45

Arg Asn Val Tyr Asn Lys Cys Cys Thr Thr Asn Leu Cys Asn Thr
50 55 60

<210> SEQ ID NO 55
<211> LENGTH: 63
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

Met Glu Cys Tyr Arg Arg Arg Ser Met His Thr Val Leu Lys Ile Thr
1 5 10 15

```
Cys Ser Ala Glu Glu Thr Phe Cys Tyr Lys Trp Leu Asn Lys Ile Ala
            20                  25                  30

Lys Asn Arg Trp Leu Gly Cys Ala Lys Thr Cys Thr Glu Ile Asp Thr
        35                  40                  45

Pro Asn Val Tyr Asn Lys Cys Cys Thr Thr Asn Leu Cys Asn Thr
    50                  55                  60


<210> SEQ ID NO 56
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Glu Cys Tyr Arg Asn Pro Arg Thr Ile Arg Ala Leu Lys Ile Thr
1               5                   10                  15

Cys Ser Ala Glu Glu Thr Phe Cys Tyr Lys Trp Leu Asn Lys Asp Leu
            20                  25                  30

Ala Glu Arg Trp Leu Gly Cys Ala Lys Thr Cys Thr Glu Ile Asp Asn
        35                  40                  45

Gln Asn Val Tyr Asn Lys Cys Cys Thr Thr Asn Leu Cys Asn Thr
    50                  55                  60


<210> SEQ ID NO 57
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(12)
<223> OTHER INFORMATION: Any amino acid
<220> FEATURE:
<221> NAME/KEY: MOD_RES
<222> LOCATION: (30)..(33)
<223> OTHER INFORMATION: This region may encompass 'GTRQ', 'NPSH',
      'PGNT', 'KLPR', 'TIPA', 'IAKN' or 'DLAE'
<220> FEATURE:
<221> NAME/KEY: MOD_RES
<222> LOCATION: (47)..(48)
<223> OTHER INFORMATION: This region may encompass 'PP', 'NR', 'TQ',
      'KP', 'ER', 'TP' or 'NQ'
<220> FEATURE:
<223> OTHER INFORMATION: See specification as filed for detailed
      description of substitutions and preferred embodiments

<400> SEQUENCE: 57

Met Glu Cys Tyr Arg Xaa Xaa Xaa Xaa Xaa Xaa Leu Lys Ile Thr Cys
1               5                   10                  15

Ser Ala Glu Glu Thr Phe Cys Tyr Lys Trp Leu Asn Lys Xaa Xaa Xaa
            20                  25                  30

Xaa Arg Trp Leu Gly Cys Ala Lys Thr Cys Thr Glu Ile Asp Xaa Xaa
        35                  40                  45

Asn Val Tyr Asn Lys Cys Cys Thr Thr Asn Leu Cys Asn Thr
    50                  55                  60


<210> SEQ ID NO 58
<211> LENGTH: 63
<212> TYPE: PRT
<213> ORGANISM: Artificial Sequence
<220> FEATURE:
```

-continued

```
<223> OTHER INFORMATION: Description of Artificial Sequence: Synthetic
      polypeptide

<400> SEQUENCE: 58

Met Glu Cys Tyr Arg Cys Gly Val Ser Gly Cys His Leu Lys Ile Thr
1               5                   10                  15

Cys Ser Ala Glu Glu Thr Phe Cys Tyr Lys Trp Leu Asn Lys Ile Ser
            20                  25                  30

Asn Glu Arg Trp Leu Gly Cys Ala Lys Thr Cys Thr Glu Ile Asp Thr
        35                  40                  45

Trp Asn Val Tyr Asn Lys Cys Cys Thr Thr Asn Leu Cys Asn Thr
    50                  55                  60
```